(12) United States Patent
Iwanowicz

(10) Patent No.: US 11,091,477 B2
(45) Date of Patent: Aug. 17, 2021

(54) PROTEIN KINASE REGULATORS

(71) Applicant: Madera Therapeutics, LLC, Cary, NC (US)

(72) Inventor: Edwin J. Iwanowicz, Cary, NC (US)

(73) Assignee: Madera Therapeutics, LLC, Cary, NC (US)

( * ) Notice: Subject to any disclaimer, the term of this patent is extended or adjusted under 35 U.S.C. 154(b) by 0 days.

(21) Appl. No.: 16/324,741

(22) PCT Filed: Aug. 14, 2017

(86) PCT No.: PCT/US2017/046727
§ 371 (c)(1),
(2) Date: Feb. 11, 2019

(87) PCT Pub. No.: WO2018/031990
PCT Pub. Date: Feb. 15, 2018

(65) Prior Publication Data
US 2020/0181139 A1 Jun. 11, 2020

Related U.S. Application Data

(60) Provisional application No. 62/374,455, filed on Aug. 12, 2016.

(51) Int. Cl.
*C07D 471/04* (2006.01)
*C07D 239/52* (2006.01)
*A61K 31/505* (2006.01)
*A61P 35/00* (2006.01)
*A61P 35/04* (2006.01)

(52) U.S. Cl.
CPC ............ *C07D 471/04* (2013.01); *A61P 35/04* (2018.01)

(58) Field of Classification Search
CPC .. C07D 471/04; C07D 239/52; A61K 31/505; A61P 35/00
See application file for complete search history.

(56) References Cited

U.S. PATENT DOCUMENTS 5,556,854 A * 9/1996 Furrer .................. C07D 471/04
514/234.2
8,318,751 B2 * 11/2012 Boyle ..................... A61P 27/02
514/264.1

* cited by examiner

*Primary Examiner* — Bruck Kifle
(74) *Attorney, Agent, or Firm* — Lewis Kohn & Walker LLP; David M. Kohn

(57) ABSTRACT

Novel compounds and pharmaceutically acceptable salts capable of modulating the activity of kinases, including Akt, ERK and MEK. Such modulation affects biological functions, for example, by inhibiting cell proliferation and/or inducing apoptosis. Also provided are pharmaceutical compositions and medicaments, comprising the compounds or salts of the invention, alone or in combination with other therapeutic agents or palliative agents.

21 Claims, 1 Drawing Sheet

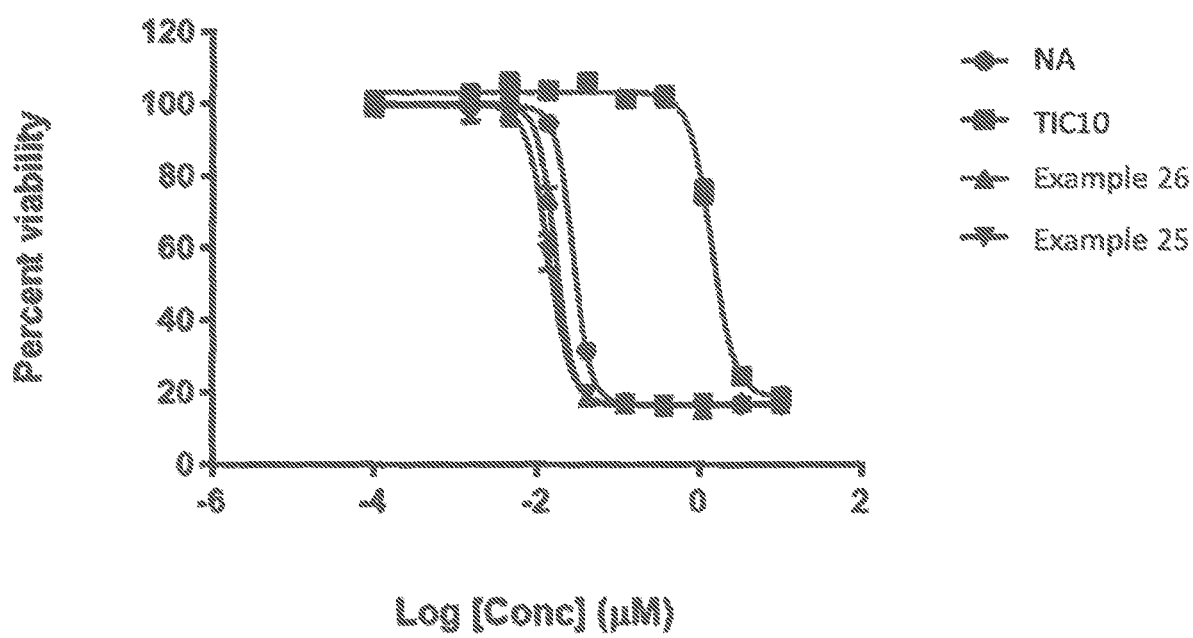

PROTEIN KINASE REGULATORS

FIELD OF THE INVENTION

The present invention relates to nitrogen containing cyclic compounds and salts thereof, to methods of using such compounds in treating diseases and disorders related to abnormal cell proliferation such as immunological and oncological disorders, and to the pharmaceutical compositions containing such compounds.

BACKGROUND OF THE INVENTION

Kinase signaling pathways, often upregulated in cancer, have been shown to drive many of the hallmark phenotypes of tumor biology. See Hoeflich et al., *J. Clin. Invest.* 2016, 125(5): 1780-1788, and references cited therein. Modulating kinase signaling through direct interaction of a drug with a kinase has led to more than 25 oncology drugs targeting kinases being approved. However, resistance often develops to kinase inhibitors directed toward a single kinase (target kinase) in a biological pathway. Most often the resistance is due to the rise of variants, with advantageous (pro-survival) mutations in the target kinase, and through a more recently appreciated phenomenon of reprogramming of the kinome. See Johnson et al., *Clin. Pham. & Thera.* 2014 95(4) 413-415 and references cited therein. Recently, inactivation of kinases, Akt, ERK and MEK, by a small molecule agent, TIC10 (11-benzyl-7-[(2-methylphenyl)methyl]-2,5,7,11-tetraazatricyclo[7.4.0.0$^{2,6}$]trideca-1(9),5-dien-8-one), was shown to activate the transcription factor, Foxo3a. See EI-Deiry et al., *Sci Transl Med* 2013, 5 171ra117 and references cited therein and EI-Deiry et al., *Cancer Res.* 2015 75(7) 1423-1432 and references cited therein. Foxo3a, a member of the Forkhead Box family of transcription factors, regulates the production of Bim (BCL-like protein 11), FasL (Fas ligand/CD95L), TRAIL (TNF-related apoptosis-inducing factor), PUMA (p53 upregulated modulator of apoptosis), p27 (cyclin-dependent kinase inhibitor 1B) and p21 (cyclin-dependent kinase inhibitor 1). These are regulatory factors in cell growth arrest and apoptosis, and upregulating these factors has utility in treating abnormal cell proliferation and in particular cancer. Thus, small molecule regulators of Foxo3a activation, via the regulation of Akt and ERK activity, are useful in the treatment of cancer. See Jiang et al., *Biochem. Biophys. Res. Commun.* 2016 476(4) 260-266 and references cited therein and Taylor et al. *Cancer Cell Inter.* 2015 15(1) 1-9, and references cited therein. Two recent patent publications, US 2014/0335048 and WO 2015/153468 describe compounds that regulate TRAIL.

SUMMARY OF THE INVENTION

The present invention provides, in part, novel compounds and pharmaceutically acceptable salts. Such compounds may modulate the activity the kinases: Akt, ERK and MEK thereby affecting biological functions, for example by inhibiting cell proliferation and/or inducing apoptosis. Also provided are pharmaceutical compositions and medicaments, comprising the compounds or salts of the invention, alone or in combination with other therapeutic agents or palliative agents. The present invention also provides, in part, methods for preparing the novel compounds, salts and compositions thereof, and methods of using the foregoing.

One aspect of the invention is directed to a compound having a pharmacophore represented by Formula (I):

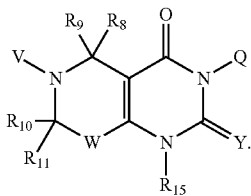

(I)

In Formula I, Q may be independently selected from the group consisting of heteroaryl;

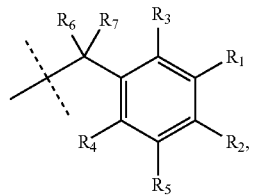

M1

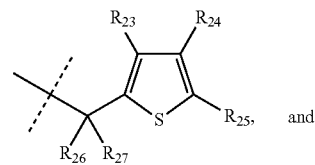

M2

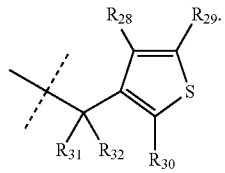

M3 and

Further, V may be independently selected from the group consisting of:

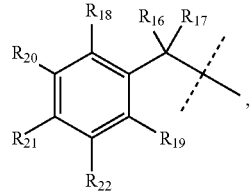

V1

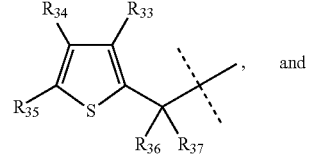

V2 and

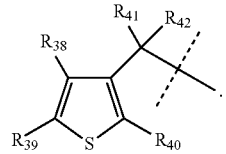

V3

Further, W may be absent or —C($R_{12}R_{13}$)—. Y may be independently selected from the group consisting of oxygen, sulphur, and —NR$_{14}$. R$_1$, R$_2$, R$_3$, R$_4$, and R$_5$ may be independently selected from the group consisting of hydrogen, halogen, —CN, —S(O)$_2$R$_{43}$, —NO$_2$, —NR$_{44}$R$_{45}$, —OH, —SH, —SR$_{46}$, (C1-C3)haloalkyloxy, (C1-C4) alkoxy, (C1-C6)alkyl, (C3-C6)cycloalkyl, (C2-C6)alkynyl, (C2-C6)alkenyl and (C1-C6)haloalkyl; or alternatively, R$_1$ and R$_2$ may be taken together with the carbon atoms to which they are attached to form a 4-6 membered ring. R$_{23}$, R$_{24}$, R$_{25}$, R$_{28}$, R$_{29}$ and R$_{30}$ may be independently selected from the group consisting of hydrogen, halogen, —CN, —S(O)$_2$R$_{43}$, —NO$_2$, —NR$_{44}$R$_{45}$, —OH, —SH, —SR$_{46}$, (C1-C3)haloalkyloxy, (C1-C4)alkoxy, (C1-C6)alkyl, (C3-C6)cycloalkyl, (C2-C6)alkynyl, (C2-C6)alkenyl and (C1-C6)haloalkyl; or alternatively, R$_{24}$ and R$_{25}$ may be taken together with the carbon atoms to which they are attached to form a ring. R$_{28}$ and R$_{29}$ may be taken together with the carbon atoms to which they are attached to form a ring. R$_6$, R$_7$, R$_8$, R$_9$, R$_{10}$, R$_{11}$, R$_{12}$, R$_{13}$, R$_{16}$, R$_{17}$, R$_{26}$, R$_{27}$, R$_{31}$, R$_{32}$, R$_{36}$, R$_{37}$, R$_{41}$, and R$_{42}$ are each independently selected from the group consisting of hydrogen, halogen, —CN, —S(O)$_2$R$_{43}$, —NO$_2$, —NRR, —OH, —SH, —SR$_{46}$, (C1-C3)haloalkyloxy, (C1-C4)alkoxy, (C1-C6)alkyl, (C3-C6)cycloalkyl, (C2-C6)alkynyl, (C2-C6)alkenyl and (C1-C6)haloalkyl. R$_{14}$ and R$_{15}$ may be independently selected from the group consisting of hydrogen, halogen, —CN, —S(O)$_2$R$_{43}$, —NO$_2$, —NR$_{44}$R$_{45}$, —OH, —SH, —SR$_{46}$, —S(O)$_2$R$_{43}$, (C1-C3)haloalkyloxy, (C1-C4)alkoxy, (C1-C6)alkyl, (C3-C6)cycloalkyl, (C2-C6)alkynyl, (C2-C6)alkenyl and (C1-C6)haloalkyl, —C(NH)NH$_2$, —C(O)R$_{43}$, —C(O)OR$_{46}$. R$_{18}$, R$_{19}$, R$_{20}$, R$_{21}$, and R$_{22}$ may be independently selected from the group consisting of the following: hydrogen, halogen, (C1-C6)alkyl, (C3-C9)cycloalkyl, (C3-C9)cycloalkyl(C1-C6)alkyl, (C1-C6)haloalkyl, —OH, —SH, (C1—C6)alkoxy, —NR$_{44}$R$_{45}$, (C3-C9)cycloalkyl(C2-C6)alkynyl, (C4-C8)cycloalkenyl, (C4-C8)cycloalkenyl(C1-C6)alkyl, aryl, heteroaryl, heterocyclyl, —CN, —NO$_2$, —SR$_{46}$, —C(O)OH, —C(O)OR$_{46}$, —OC(O)OR$_{46}$, (C2-C6)alkynyl, (C2-C8)alkenyl, (C1-C6)haloalkyoxy, —S(O)$_2$OR$_{46}$, —SO$_2$NR$_{44}$R$_{45}$, —S(O)$_2$R$_{43}$, —NR$_{47}$S(O)$_2$R$_{43}$, —C(O)NR$_{44}$R$_{45}$, —C(O)R$_{43}$, and —NR$_{47}$C(O)R$_{43}$; or alternatively, R$_{20}$ and R$_{21}$ may be taken together with the carbon atoms to which they are attached to form a ring. R$_{33}$, R$_{34}$, R$_{35}$, R$_{38}$, R$_{39}$ and R$_{40}$ may be independently selected from the group consisting of the following: hydrogen, halogen, (C1-C6)alkyl, (C3-C9)cycloalkyl, (C3-C9)cycloalkyl(C1-C6)alkyl, (C1-C6)haloalkyl, —OH, —SH, (C1-C6)alkoxy, —NR$_{44}$R$_{45}$, (C3-C9)cycloalkyl(C2-C6)alkynyl, (C4-C8)cycloalkenyl, (C4-C8)cycloalkenyl(C1-C6)alkyl, aryl, heteroaryl, heterocyclyl, —CN, —NO$_2$, —SR$_{46}$, —C(O)OH, —C(O)OR$_{46}$, —OC(O)OR$_{46}$, (C2-C6)alkynyl, (C2-C8)alkenyl, (C1-C6)haloalkyoxy, —S(O)$_2$OR$_{46}$, —SO$_2$NR$_{44}$R$_{45}$, —S(O)$_2$R$_{43}$, —NR$_{47}$S(O)$_2$R$_{43}$, —C(O)NR$_{44}$R$_{45}$, —C(O)R$_{43}$, and —NR$_{47}$C(O)R$_{43}$; or alternatively, R$_{34}$ and R$_{35}$ may be taken together with the carbon atoms to which they are attached to form a ring. R$_{38}$ and R$_{39}$ may be taken together with the carbon atoms to which they are attached to form a ring. R$_{43}$ may be independently selected from the group consisting of hydrogen, (C1-C6)alkyl, (C3-C9)cycloalkyl, (C1-C6)haloalkyl, (C2-C6)alkynyl, (C2-C8)alkenyl, (C1-C6)haloalkyoxy, aryl, heteroaryl, heterocyclyl and —NR$_{44}$R$_{45}$. R$_{44}$, R$_{45}$ and R$_{47}$ may be independently selected from the group consisting of hydrogen, (C1-C6)alkyl, (C3-C9)cycloalkyl, (C1-C6)haloalkyl, (C2-C6)alkynyl, (C2-C8)alkenyl, (C1-C6)haloalkyoxy, aryl, heteroary and heterocyclyl; R$_{44}$ and R$_{45}$ together with the nitrogen atom to which they are attached may form a ring. R$_{46}$ may be independently selected from the group consisting of hydrogen, (C1-C6) alkyl, (C3-C9)cycloalkyl, (C1-C6)haloalkyl, (C2-C6)alkynyl, (C2-C8)alkenyl, (C1-C6)haloalkyoxy, aryl, heteroaryl and heterocyclyl. Or, alternatively, the compound may include a pharmaceutically acceptable salt thereof.

In a first preferred embodiment of the first aspect of the invention, the substituent Y in Formula I is oxygen. In a second preferred embodiment, the substituent Q in Formula I is M1; V is V1; and R$_{15}$ is independently selected from the group consisting of hydrogen, —CN, —S(O)$_2$R$_{43}$, —NO$_2$, —NR$_{44}$R$_{45}$, —OH, —SR$_{46}$, —S(O)$_2$R$_{43}$, (C1-C3)haloalkyloxy, (C1-C4)alkoxy, (C1-C6)alkyl, (C3-C6)cycloalkyl, (C2-C6)alkynyl, (C2-C6)alkenyl and (C1-C6)haloalkyl, —C(NH)NH$_2$, —C(O)R$_{43}$, —C(O)OR$_{46}$. In a third preferred embodiment, R$_1$ is independently selected from hydrogen, fluorine and chlorine; R$_2$ is independently selected from chlorine, bromine and —CF$_3$; R$_3$ is independently selected from hydrogen and fluorine; R$_{15}$ is independently selected from —CH$_3$ and —CH$_2$CH$_3$; R$_{20}$ is —CN; and R$_4$, R$_5$, R$_6$, R$_7$, R$_8$, R$_9$, R$_{10}$, R$_{11}$, R$_{16}$, R$_{17}$, R$_{18}$, R$_{19}$, R$_{21}$, R$_{22}$ are simultaneously hydrogen. In a fourth preferred embodiment, the compound may be independently selected from the group of compounds consisting of the following:

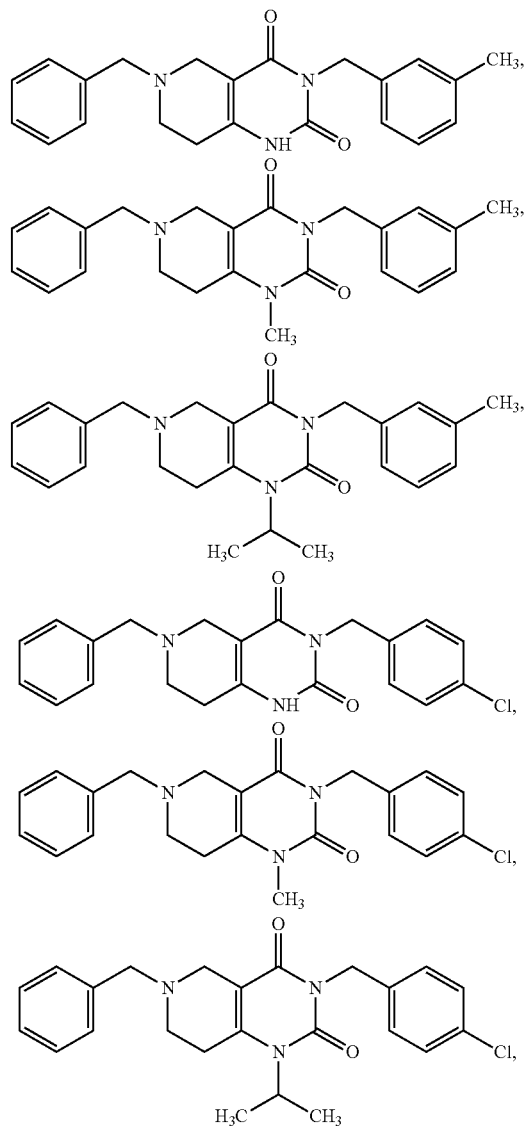

-continued
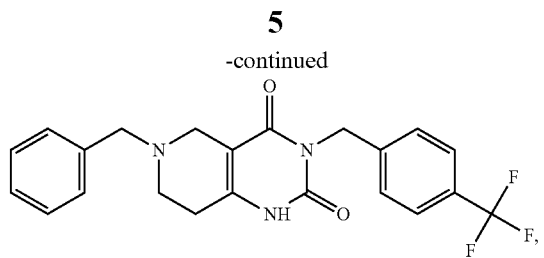
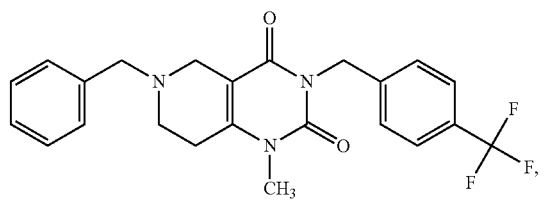
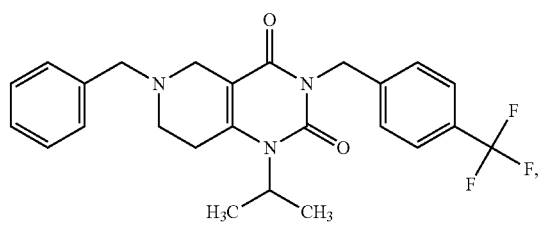
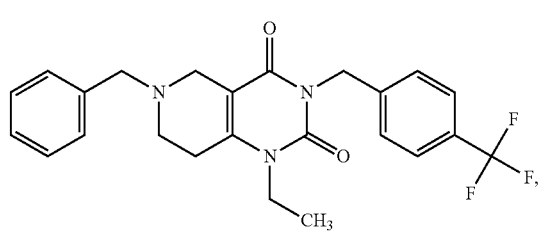
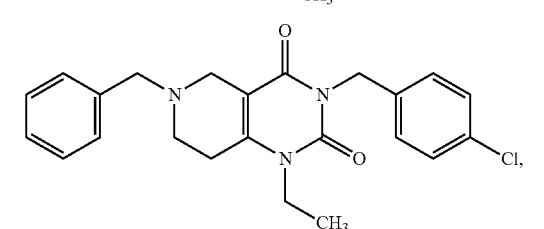
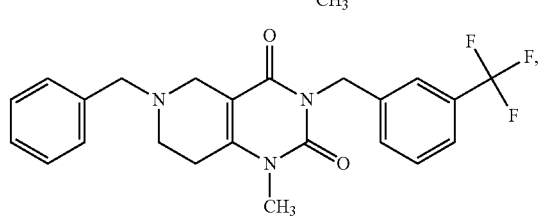
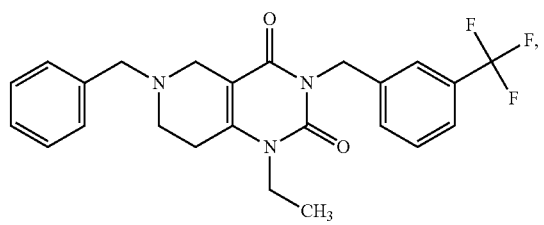
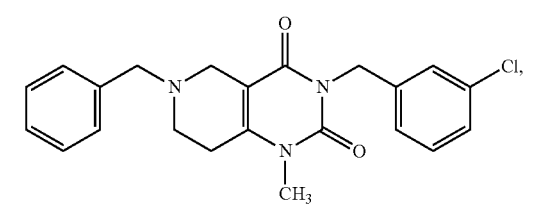
-continued
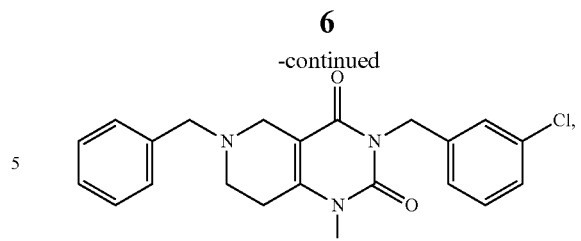
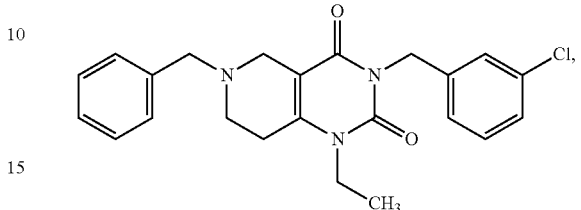
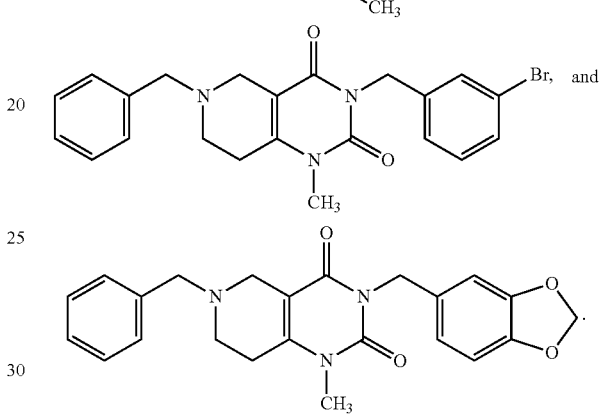
In a fifth preferred embodiment, the compound may be independently selected from the group of compounds consisting of the following:
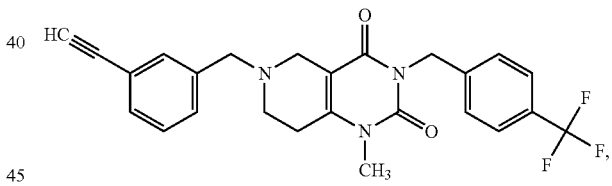
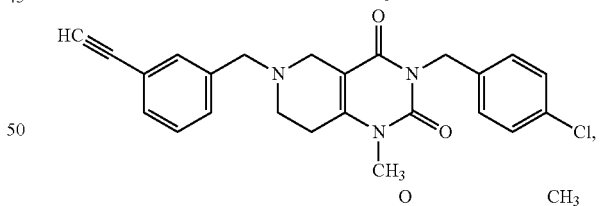
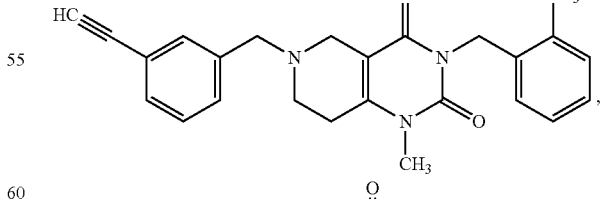
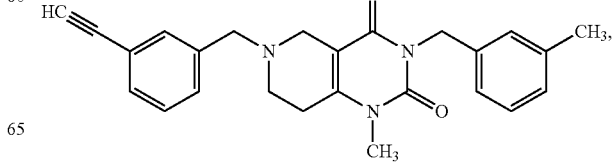

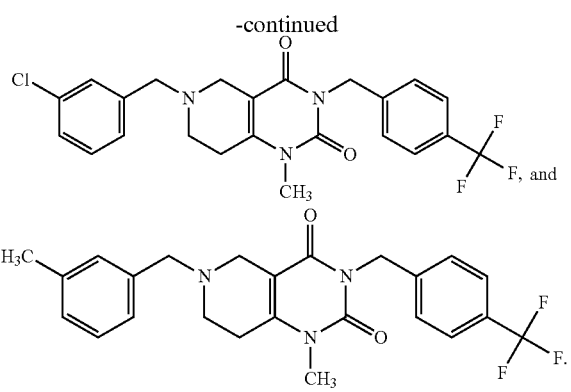

In a sixth preferred embodiment, the compound may be independently selected from the group of compounds consisting of the following:

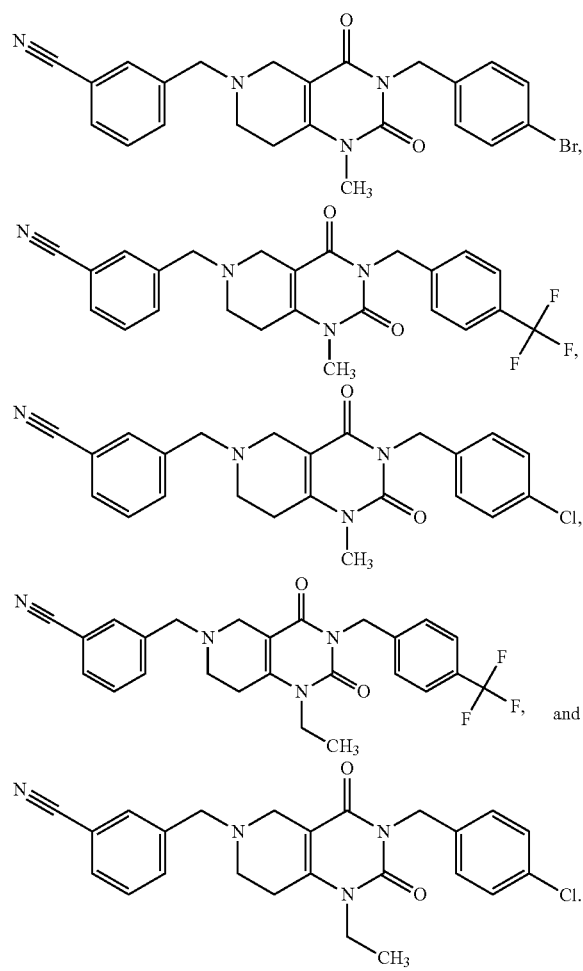

Each of the embodiments herein describing the invention envisions within the scope the pharmaceutically acceptable salts of the compounds of the invention. Accordingly, the phrase "or a pharmaceutically acceptable salt thereof" is implicit in the description of all compounds described herein.

A second aspect of the invention is directed to a method for the treatment of cancer in a subject comprising the step of administering an effective amount of a compound of Formula I, or a pharmaceutically acceptable salt thereof. In a first preferred mode of the second aspect of the invention, the method for the treatment of cancer in a subject comprises the step of administering an effective amount of a compound of the first preferred embodiment of Formula I, or a pharmaceutically acceptable salt thereof. In a first preferred mode of the second aspect of the invention, the method for the treatment of cancer in a subject comprises the step of administering an effective amount of a compound of the first preferred embodiment of Formula I, or a pharmaceutically acceptable salt thereof. In a second preferred mode of the second aspect of the invention, the method for the treatment of cancer in a subject comprises the step of administering an effective amount of a compound of the second preferred embodiment of Formula I, or a pharmaceutically acceptable salt thereof. In a third preferred mode of the second aspect of the invention, the method for the treatment of cancer in a subject comprises the step of administering an effective amount of a compound of the third preferred embodiment of Formula I, or a pharmaceutically acceptable salt thereof. In a fourth preferred mode of the second aspect of the invention, the method for the treatment of cancer in a subject comprises the step of administering an effective amount of a compound of the fourth preferred embodiment of Formula I, or a pharmaceutically acceptable salt thereof. In a fifth preferred mode of the second aspect of the invention, the method for the treatment of cancer in a subject comprises the step of administering an effective amount of a compound of the fifth preferred embodiment of Formula I, or a pharmaceutically acceptable salt thereof. In a sixth preferred mode of the second aspect of the invention, the method for the treatment of cancer in a subject comprises the step of administering an effective amount of a compound of the sixth preferred embodiment of Formula I, or a pharmaceutically acceptable salt thereof.

In frequent embodiments of the methods provided herein, the abnormal cell growth is cancer. In some embodiments, the methods provided result in one or more of the following: (1) inhibiting cancer cell proliferation; (2) inhibiting cancer cell invasiveness; (3) inducing apoptosis of cancer cells; (4) inhibiting cancer cell metastasis; or (5) inhibiting angiogenesis.

In frequent embodiments, the abnormal cell growth is cancer and the subject is a human.

In some embodiments, the methods described herein further comprise administering to the subject an amount of an anti-cancer therapeutic agent or a palliative agent, which amounts may be together effective in treating said abnormal growth. In some embodiments, the one or more anti-cancer therapeutic agent is selected from anti-tumor agents, anti-angiogenesis agents, signal transduction inhibitors, and anti-proliferative agents, which amounts are together effective in treating said abnormal cell growth. In some such embodiments, the anti-tumor agent is selected from the group consisting of mitotic inhibitors, alkylating agents, antimetabolites, intercalating antibodies, growth factor inhibitors, radiation, cell cycle inhibitors, enzymes, topoisomerase inhibitors, biological response modifiers, antibodies, cytotoxics, anti-hormones, and anti-androgens.

A third aspect of the invention is directed to a pharmaceutical composition comprising a compound represented by Formula I, or a pharmaceutically acceptable salt thereof, in combination with a pharmaceutically acceptable carrier or excipient. In a first preferred embodiment of this third aspect of the invention, the pharmaceutical composition comprises a compound of the first preferred embodiment of Formula I, or a pharmaceutically acceptable salt thereof, in combination with a pharmaceutically acceptable carrier or excipient. In a second preferred embodiment of this third aspect of the invention, the pharmaceutical composition comprises a compound of the second preferred embodiment of Formula I, or a pharmaceutically acceptable salt thereof, in combination with a pharmaceutically acceptable carrier or excipient. In a third preferred embodiment of this third aspect of the invention, the pharmaceutical composition comprises a compound of the third preferred embodiment of Formula I, or a pharmaceutically acceptable salt thereof, in combination with a pharmaceutically acceptable carrier or excipient. In a fourth preferred embodiment of this third aspect of the invention, the pharmaceutical composition comprises a compound of the fourth preferred embodiment of Formula I, or a pharmaceutically acceptable salt thereof, in combination with a pharmaceutically acceptable carrier or excipient. In a fifth preferred embodiment of this third aspect of the invention, the pharmaceutical composition comprises a compound of the fifth preferred embodiment of Formula I, or a pharmaceutically acceptable salt thereof, in combination with a pharmaceutically acceptable carrier or excipient. In a sixth preferred embodiment of this third aspect of the invention, the pharmaceutical composition comprises a compound of the sixth preferred embodiment of Formula I, or a pharmaceutically acceptable salt thereof, in combination with a pharmaceutically acceptable carrier or excipient. In some embodiments, the pharmaceutical composition comprises two or more pharmaceutically acceptable carrier and/or excipient.

BRIEF DESCRIPTION OF DRAWING

FIG. 1 illustrates a graph depicting biological activity data on a human cancer cell line.

DETAILED DESCRIPTION OF THE INVENTION

The present invention may be understood more readily by reference to the following detailed description of the preferred embodiments of the invention and the Examples included herein.

Definitions

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the structure. If a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" portions of "hydroxyalkyl," "fluoroalkyl," "—O-alkyl," etc.

As used herein, and throughout this disclosure, the following terms, unless otherwise indicated, shall be understood to have the following meanings:

A "patient" or "subject" is a human or non-human mammal. In one embodiment, a patient or subject is a human. In another embodiment, a patient or subject is a chimpanzee.

The term "therapeutically effective amount" as used herein, refers to an amount of the compound of Formula (I) and/or additional therapeutic agent, or a composition thereof that is effective in producing the desired therapeutic, ameliorative, inhibitory or preventative effect when administered to a patient suffering from cancer or another disease or disorder of undesirable cell proliferation. In the combination therapies of the present invention, a therapeutically effective amount can refer to each individual agent or to the combination as a whole, wherein the amounts of all agents administered are together effective, but wherein the component agent of the combination may not be present individually in an effective amount. In reference to the treatment of cancer, a therapeutically effective amount, refers to that amount which has the effect of (1) reducing the size of the tumor, (2) inhibiting (that is slowing to some extent, preferably stopping) tumor metastasis, (3) inhibiting to some extent (preferably stopping) tumor growth or tumor invasiveness and/or (4) relieving to some extent (or preferably, eliminating) one or more signs or symptoms associated with cancer.

The term "preventing" as used herein with respect to cancer or a disease or disorder of undesirable cell proliferation, refers to reducing the likelihood or rate of disease or disorder progression.

The use of a dashed or dotted line signifies a single bond between said molecular fragment and another defined molecular fragment. For example, the selection of V1 for V in Formula (I) yields the following structure:

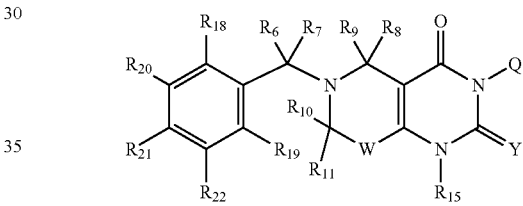

In another example, the selection of M1 for Q in Formula (I) yields the following structure:

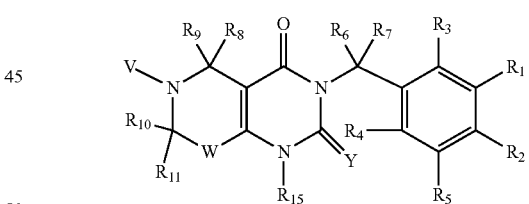

The term "alkyl" as used herein, refers to an aliphatic hydrocarbon group having one of its hydrogen atoms replaced with a bond having the specified number of carbon atoms. The alkyl group may be straight chain or branched chain groups. In addition to the term "alkyl", alkyl groups may be further defined by the number of carbon atom. Alkyl substituents typically contain 1 to 20 carbon atoms "(C1-C20)alkyl", preferably 1-12 carbon atoms "(C1-C12)alkyl", more preferably 1 to 8 carbon atoms "(C1-C8)alkyl", or 1 to 6 carbon atoms "(C1-C6)alkyl", or 1 to 4 carbon atoms "(C1-C4)alkyl". In different embodiments, an alkyl group contains from 7-12 carbon atoms "(C7-C12)alkyl" or from 7 to 20 carbon atoms "(C7-C20)alkyl". Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. All alkyl groups described herein may be optionally substituted by one or more substituent groups, which are selected independently unless otherwise indicated. Alkyl groups described herein as substituted alkyl ("substituted alkyl") will be substituted with one or more substituent groups, which are selected independently unless otherwise indicated. The total number of substituent groups may equal the total number of hydrogen atoms on the alkyl moiety, to the extent such substitution makes chemical sense. Optionally substituted alkyl groups typically contain from 1 to 6 optional substituents, preferably from 1 to 4 optional substituents and more preferably from 1 to 3 optional substituents. For example, an optionally substituted ethylene group is "optionally substituted (C2)alkyl" and a substituted ethylene group is "substituted (C2)alkyl".

Suitable substituent groups for alkyl, "alkyl", "optionally substituted alkyl" and "substituted alkyl" include, but are not limited to (C3-C8)cycloalkyl, 3-12 membered heterocyclyl, (C6-C12)aryl, 5-12 membered heteroaryl, halo, =O (oxo), =S (thiono), =N—CN, =N—OR$^X$, =NR$^X$, —CN, —C(O)R$^X$, —CO$_2$R$^X$, —C(O)NR$^X$R$^Y$, —SR$^X$, —SOR$^X$, —SO$_2$R$^X$, —SO$_2$NR$^X$R$^Y$, —NO$_2$, —NR$^X$R$^Y$, —NR$^X$C(O) R$^Y$, —NR$^X$C(O)NR$^X$R$^Y$, —NR$^X$C(O)OR$^X$, —NR$^X$SO$_2$R$^Y$, —NR$^X$SO$_2$NR$^X$R$^Y$, —OR$^X$, —OC(O)R$^X$ and —OC(O) NR$^X$R$^Y$; where in each R$^X$ and R$^Y$ is independently hydrogen, (C1-C6)alkyl, (C2-C6)alkenyl, (C2-C6)alkynyl, (C3-C6)cycloalkyl, 3-12 membered heterocyclyl, (C6-C12)aryl, or 5-12 membered heteroaryl, or R$^X$ and R$^Y$ may be taken together with the nitrogen atom to which they are attached to form a 3-12 membered heterocyclyl or 5-12 membered heteroaryl system, each optionally containing 0, 1 or 2 additional heteroatoms; each R$^X$ and R$^Y$ is optionally substituted with 1 to 3 substituents independently selected from the group consisting of halo, =O, —CN, —C(O)R', —CO$_2$R', —C(O)NR'$_2$, —SO$_2$R', —NR'$_2$, —OR', wherein each R' is independently hydrogen, (C1-C6)alkyl, (C3-C6)cycloalkyl, or 3-12 membered heterocyclyl. However, suitable substituent for "substituted alkyl" does not include hydrogen.

"Alkenyl" refers to an alkyl group, as defined herein, consisting of at least two carbon atoms and at least one carbon-carbon bond. Typically, alkenyl groups have 2 to 20 carbon atoms "(C2-C20)alkenyl", preferably 2 to 12 carbon atoms "(C2-C12)alkenyl", more preferably 2 to 8 carbon atoms "(C2-C8)alkenyl", or 2 to 6 carbon atoms "(C2-C6) alkenyl", or 2 to 4 carbon atoms "(C2-C4)alkenyl". Representative examples include, but are not limited to, ethenyl, 1-propenyl, 2-propenyl, 1-, 2-, or 3-butenyl, and the like. An alkenyl group may be optionally substituted. Suitable substituent groups for alkenyl are as described herein for, "optionally substituted alkyl", "substituted alkyl" and alkyl.

"Alkynyl" refers to an alkyl group, as defined herein, consisting of at least two carbon atoms and at least one carbon-carbon triple bond. Alkynyl groups have 2 to 20 carbon atoms "(C2-C20)alkynyl", preferably 2 to 12 carbon atoms "(C2-C12)alkynyl", more preferably 2 to 8 carbon atoms "(C2-C8)alkynyl", or 2 to 6 carbon atoms "(C2-C6) alkynyl", or 2 to 4 carbon atoms "(C2-C4)alkynyl". Representative examples include, but are not limited to, ethynyl, 1-propynyl, 2-propynyl, 1-, 2-, or 3-butynyl, and the like. Any alkynyl groups may be optionally substituted. Suitable substituent groups for alkynyl are as described herein for, "optionally substituted alkyl", "substituted alkyl" and alkyl.

The term "fluoroalkyl," as used herein, refers to an alkyl group as defined above, wherein one or more of the alkyl group's hydrogen atoms has been replaced with a fluorine. In one embodiment, a fluoroalkyl group has from 1 to 6 carbon atoms. In another embodiment, a fluoroalkyl group has from 1 to 3 carbon atoms. In another embodiment, a fluoroalkyl group is substituted with from 1 to 3 fluorine atoms. Non-limiting examples of fluoroalkyl groups include —CH$_2$F, —CHF$_2$, and —CF$_3$. The term "(C1-C3) fluoroalkyl" refers to a fluoroalkyl group having from 1 to 3 carbon atoms. The term "(C1)fluoroalkyl" refers to —CH$_2$F, —CHF$_2$, and —CF$_3$.

The term "aryl" as used herein, refers to an aromatic monocyclic or multicyclic ring system comprising from 6 to about 14 carbon atoms. In one embodiment, an aryl group contains from about 6 to 10 carbon atoms (C6-C10)aryl. In another embodiment, an aryl group is phenyl. Non-limiting examples of aryl groups include phenyl and naphthyl. Aryl groups may be optionally substituted. Suitable substituent groups for aryl are as described herein for, "optionally substituted alkyl", "substituted alkyl" and alkyl.

The term "cycloalkyl," as used herein, refers to a saturated ring containing the specified number of ring carbon atoms, and no heteroatoms. Cycloalkyl substituents typically contain 3 to 8 carbon atoms "(C3-C8)cycloalkyl", preferably 3-7 carbon atoms "(C3-C7)cycloalkyl", more preferably 3 to 6 carbon atoms "(C3-C6)cycloalkyl", or 3 to 5 carbon atoms "(C3-05)cycloalkyl". Non-limiting examples of monocyclic cycloalkyls include cyclopropyl, cyclobutyl, cyclopentyl, and cyclohexyl. All cycloalkyl groups described herein may be optionally substituted by one or more substituent groups, which are selected independently unless otherwise indicated. Cycloalkyl groups described herein as optionally substituted ("optionally substituted cycloalkyl") may be substituted by one or more substituents groups, which are selected independently unless otherwise indicated. Cycloalkyl groups described herein as substituted cycloalkyl ("substituted cycloalkyl") will be substituted with one or more substituent groups, which are selected independently unless otherwise indicated. The total number of substituent groups may equal the total number hydrogen atoms on the cycloalkyl moiety, to the extent such substitution makes chemical sense. Optionally substituted cycloalkyl groups typically contain from 1 to 6 optional substituents, preferably from 1 to 4 optional substituents and more preferably from 1 to 3 optional substituents. For example, an optionally substituted cyclopropyl group is "optionally substituted (C3)cycloalkyl" and a substituted cyclopropyl group is "substituted (C2)cycloalkyl". In one embodiment a cycloalkyl group contains 3 to 9 carbon atoms, "(C3-C9)cycloalkyl". In another embodiment a substituted cycloalkyl group contains 3 to 9 carbon atoms, "substituted (C3-C9)cycloalkyl". Suitable substituent groups for cycloalkyl are as described herein for, "optionally substituted alkyl", "substituted alkyl" and alkyl.

The term "cycloalkenyl" as used herein, refers to partially unsaturated carbocyclic ring system containing the specified number of carbon atoms. Cycloalkenyl substituents typically contain 4 to 8 carbon atoms "(C4-C8)cycloalkenyl" and preferably 5-6 carbon atoms "(C5-C6)cycloalkenyl". Non-limiting examples of monocyclic cycloalkenyls include cyclobutenyl, cyclopentenyl, cyclohexenyl, and cycloheptenyl. Cycloalkenyl groups described herein may be optionally substituted with one or more substituent groups, which are selected independently unless otherwise indicated. The total number of substituent groups may equal the total number of hydrogen atoms on the cycloalkenyl moiety, to the extent such substitution makes chemical sense. Optionally substituted cycloalkenyl groups typically contain from 1 to 6 optional substituents, preferably from 1 to 4 optional substituents and more preferably from 1 to 3 optional substituents. For example, a cyclopentenyl group is "(C5) cycloalkenyl" and an optionally substituted cyclopentenyl group is "optionally substituted (C5)cycloalkenyl". In one embodiment a cycloalkenyl group contains 4 to 8 carbon atoms, "(C4-C8)cycloalkenyl". Suitable substituent groups for cycloalkenyl are as described herein for, "optionally substituted alkyl", "substituted alkyl" and alkyl.

The term "cycloalkylalkyl" as used herein, refers to a cycloalkyl ring, typically a (C3-C9)cycloalkyl, which is connected to the base molecule through an alkylene linker of 1 to 6 carbon atoms "(C1-C6)alkylene". Cycloalkylalkyl groups are described by the number of carbon atoms in the carbocyclic ring and the number of carbon atoms in the linker. Cycloalkylalkyl groups described herein may be optionally substituted with one or more substituents groups, which are selected independently unless otherwise indicated. Cycloalkylalkyl groups described herein as optionally substituted ("optionally substituted cycloalkylalkyl") may be substituted by one or more substituent groups, which are selected independently unless otherwise indicated. Cycloalkylalkyl groups described herein as substituted cycloalkylalkyl ("substituted cycloalkylalkyl") will be substituted with one or more substituent groups, which are selected independently unless otherwise indicated. The total number of substituent groups may equal the total number of hydrogen atoms on the cycloalkylalkyl moiety, to the extent such substitution makes chemical sense. Optionally substituted cycloalkylalkyl groups typically contain from 1 to 6 optional substituents, preferably from 1 to 4 optional substituents and more preferably from 1 to 3 optional substituents. In one embodiment a cycloalkyl group contains 3 to 9 carbon atoms and the linker alkyl group contains 1 to 6 carbon atoms, "(C3-C9)cycloalkyl(C1-C6)alkyl". For example, cyclopropylethyl group is "(C3)cycloalkyl(C2)alkyl" and an optionally substituted cyclopropylethyl group is "optionally substituted (C3)cycloalkyl(C2)alkyl". In addition, a substituted cyclopropylethyl group is "substituted (C3)cycloalkyl(C2) alkyl". Suitable substituent groups for cycloalkylalkyl are as described herein for, "optionally substituted alkyl", "substituted alkyl" and alkyl.

The term "cycloalkenylalkyl" as used herein, refers to a cycloalkenyl ring, typically a (C4-C8)cycloalkenyl, which is connected to the base molecule through an alkylene linker of 1 to 6 carbon atoms "(C1-C6)alkylene". Cycloalkenylalkyl groups are described by the number of carbon atoms in the carbocyclic ring and the number of carbon atoms in the linker. Thus a "(C5)cycloalkyenyl(C1)alkyl" group is a cyclopentenyl group connected to the base molecule though a methylene group (—CH$_2$—). Cycloalkenylalkyl groups described herein may be optionally substituted with one or more substituent groups, which are selected independently unless otherwise indicated. The total number of substituent groups may equal the total number of hydrogen atoms on the cycloalkenylalkyl moiety, to the extent such substitution makes chemical sense. Optionally substituted cycloalkenylalkyl groups typically contain from 1 to 6 optional substituents, preferably from 1 to 4 optional substituents and more preferably from 1 to 3 optional substituents. In one embodiment a cycloalkenyl group contains 4 to 8 carbon atoms and the linker alkyl group contains 1 to 6 carbon atoms, "(C4-C8)cycloalkenyl(C1-C6)alkyl". For example, cyclopentenylethyl group is "(C5)cycloalkenyl(C2)alkyl" and an optionally substituted cyclopentenylethyl group is "optionally substituted (C5)cycloalkenyl(C2)alkyl". Suitable substituent groups for cycloalkenylalkyl are as described herein for, "optionally substituted alkyl", "substituted alkyl" and alkyl.

In some instances, substituted alkyl groups may be specifically named with reference to the substituent group. For example "haloalkyl" refers to an alkyl group having the specified number of carbon atoms that is substituted by one or more halo substituents, and typically contain 1 to 6 carbon atoms and 1, 2 or 3 halo atoms (i.e., "(C1-C6)haloalkyl"). Thus, a (C1-C4)haloalkyl group includes trifluoromethyl (—CF$_3$) and difluoromethyl (—CF$_2$H). Haloalkyl groups described herein may be optionally substituted with one or more substituent groups, which are selected independently unless otherwise indicated. The total number of substituent groups (the sum of the number of halo and any other substituents defined herein) may equal the total number of hydrogen atoms on the unsubstituted parent alkyl moiety, to the extent such substitution makes chemical sense. For example, for —CH$_2$CH$_2$CH(OH)CH$_2$CF$_3$ the parent alkyl moiety is N-pentyl (—(CH$_2$)$_4$CH$_3$) with 11 possible positions for substitution. This example is not meant to be limiting. Haloalkyl groups described herein as optionally substituted ("optionally substituted haloalkyl") may be substituted by one or more substituent groups, which are selected independently unless otherwise indicated. Haloalkyl groups described herein as substituted haloalkyl ("substituted haloalkyl") will be substituted with one or more substituent groups, which are selected independently unless otherwise indicated. The total number of substituent groups may equal the total number hydrogen atoms on the haloalkyl moiety, to the extent such substitution makes chemical sense. Optionally substituted haloalkyl groups typically contain from 1 to 6 optional substituents, preferably from 1 to 4 optional substituents and more preferably from 1 to 3 optional substituents. For example, an optionally substituted halopropyl group is "optionally substituted (C3)haloalkyl" and a substituted halopropyl group is "substituted (C3) haloalkyl". In one embodiment a cycloalkyl group contains 1 to 6 carbon atoms, "(C1-C6)haloalkyl". In another embodiment a substituted haloalkyl group contains 1 to 6 carbon atoms, "substituted (C1-C6)haloalkyl". Suitable substituent groups for haloalkyl are as described herein for, "optionally substituted alkyl" and "substituted alkyl".

"Alkoxy" refers to a monovalent —O-alkyl group, wherein the alkyl portion has the specified number of carbon atoms. The alkyl portion of the alkoxy group, may be straight chain or branched chain groups. Alkoxy groups typically contain 1 to 8 carbon atoms "(C1-C8)alkoxy", or 1 to 6 carbon atoms "(C1-C6)alkoxy" or 1 to 4 carbon atoms "(C1-C4)alkoxy". Non-limiting examples of alkoxy groups include methoxy, ethoxy, n-propoxy, isopropoxy, n-butoxy and t-butoxy. All alkoxy groups described herein may be optionally substituted with one or more substituent groups, which are selected independently unless otherwise indicated. Alkoxy groups described herein as optionally substituted ("optionally substituted alkoxy") may be substituted by one or more substituent groups, which are selected independently unless otherwise indicated. Alkoxy groups described herein as substituted alkoxy ("substituted alkoxy") will be substituted with one or more substituent groups, which are selected independently unless otherwise indicated. The total number of substituent groups may equal the total number of hydrogen atoms on the alkoxy moiety, to the extent such substitution makes chemical sense. Optionally substituted alkoxy groups typically contain from 1 to 6 optional substituents, preferably from 1 to 4 optional substituents and more preferably from 1 to 3 optional substituents. For example, an optionally substituted ethoxy group is "optionally substituted (C2)alkoxy" and a substituted butoxy group is "substituted (C4)alkoxy". In one embodiment an alkoxy group contains 1 to 6 carbon atoms, "(C1-C6)alkoxy". In another embodiment a substituted alkoxy group contains 1 to 6 carbon atoms, "substituted (C1-C6) alkoxy". Suitable substituent groups for alkoxy are as described herein for, "optionally substituted alkyl", "substituted alkyl" and alkyl.

"Cycloalkoxy" refers to a monovalent —O-cycloalkyl group, wherein the cycloalkyl portion has the specified number of carbon atoms. The cycloalkyl portion of the alkoxy group, typically contain 3 to 9 carbon atoms "(C3-C9)cycloalkoxy", or 3 to 6 carbon atoms "(C3-C6)cycloalkoxy". Non-limiting examples of cycloalkoxy groups include cyclopropoxy, cyclobutoxy and cyclopentoxy. All cycloalkoxy groups described herein may be optionally substituted with one or more substituent groups, which are selected independently unless otherwise indicated. The total number of substituent groups may equal the total number of hydrogen atoms on the cycloalkoxy moiety, to the extent such substitution makes chemical sense. Optionally substituted cycloalkoxy groups typically contain from 1 to 6 optional substituents, preferably from 1 to 4 optional substituents and more preferably from 1 to 3 optional substituents. Suitable substituent groups for cycloalkoxy are as described herein for, "optionally substituted alkyl", "substituted alkyl" and alkyl.

The term "haloalkoxy" refers to a monovalent —O-haloalkyl group wherein the alkyl portion has the specified number of carbon atoms that are substituted by one or more halo substituents, and typically contain 1 to 6 carbon atoms and 1, 2 or 3 halo atoms (i.e., "(C1-C6)haloalkoxy") In some instances, substituted alkyl groups may be specifically named with reference to the substituent group. For example "haloalkoxy" refers to an alkyl group having the specified number of carbon atoms. Thus, a (C1-C4)haloalkoxy group includes trifluoromethoxy (—OCF$_3$). Haloalkoxy groups described herein may be substituted by one or more substituent groups, which are selected independently unless otherwise indicated. The total number of substituent groups may equal the total number of hydrogen atoms on the haloalkyl moiety, to the extent such substitution makes chemical sense. Optionally substituted haloalkoxy groups typically contain from 1 to 3 optional substituents and preferably from 1 to 2 optional substituents. In one embodiment a haloalkoxy group contains 1 to 6 carbon atoms, "(C1-C6)haloalkoxy". An example of a substituted haloalkoxy group contains 1 to 6 carbon atoms, "(C1-C6) haloalkoxy". Suitable substituent groups for haloalkyloxy are as described herein for, "optionally substituted alkyl" and "substituted alkyl".

The term "halo" as used herein, means —F, —Cl, —Br or —I. In one embodiment, a halo group is —Cl. In another embodiment, a halo group is —Br.

The term "halogen" as used herein, means —F, —Cl, —Br or —I. In one embodiment, a halogen group is —Cl. In another embodiment, a halogen group is —Br.

The term "acyl" as used herein means —C(O)alkyl or —C(O)cycloalkyl. The alkyl group may be straight chain or branched chain groups. Alkyl substituent of an acyl group typically contain 1 to 20 carbon atoms, preferably 1-12 carbon atoms, more preferably 1 to 8 carbon atoms, 1 to 6 carbon atoms, or 1 to 4 carbon atoms. The cycloalkyl substituent of an acyl group typically contain 3 to 8 carbon atoms, preferably 3-7 carbon atoms, more preferably 3 to 6 carbon atoms, or 3 to 5 carbon atoms. The alkyl and cycloalkyl moieties of an acyl group may be substituted. Suitable substituent groups are as described herein for, "optionally substituted alkyl", "substituted alkyl" and alkyl.

The term "aryl" or "aromatic" refer to an optionally substituted monocyclic biaryl or fused bicyclic ring systems, having the well-known characteristics of aromaticity, wherein at least one ring contains a completely conjugated pi-electron system. Typically, aryl groups contain 6 to 20 carbon atoms, "(C6-20)aryl" as ring members, preferably 6 to 14 carbon atoms "(C6-C14)aryl" or more preferably 6 to 12 carbon atoms "(C6-C12)aryl". Fused aryl groups may include an aryl ring (e.g., a phenyl ring) fused to another aryl ring, or fused to a saturated or partially unsaturated carbocyclic or heterocyclic ring. The point of attachment to the base molecule on such fused aryl ring systems may be a carbon atom of the aromatic portion or a carbon or nitrogen atom of the non-aromatic portion of the ring system. Example, without limitation, of aryl groups include phenyl, biphenyl, naphthyl, anthracenyl, phenanthrenyl, indanyl, indenyl, and tetrahydronaphthyl. Aryl groups described herein may be optionally substituted with one or more substituents groups, which are selected independently unless otherwise indicated. Suitable substituent groups for the aryl group are further described herein.

The term "heteroaryl" or heteroaromatic" may be used interchangeably herein, to refer to an aromatic monocyclic or multicyclic ring system comprising about 5 to about 14 ring atoms, wherein from 1 to 4 of the ring atoms is independently N, O, or S and the remaining ring atoms are carbon atoms. These systems having the well-known characteristics of aromaticity. Heteroaryl rings are attached to the base molecule via a ring atom of the heteroaromatic ring, such that aromaticity is maintained. The inclusion of a heteroatom permits aromaticity in 5-membered rings as well as 6 membered rings. In one embodiment, a heteroaryl group has 5 to 10 ring atoms. In another embodiment, a heteroaryl group is a monocyclic ring system and has 5 to 6 ring atoms. In another embodiment, a heteraryl group is a bicyclic ring system. The term "heteroaryl" also includes a heteroaryl, as defined above, fused to a heterocyclyl as defined below. The term "heteroaryl" also encompasses a heteroaryl group, as defined above, which is fused to a benzene, a cyclohexadiene or a cyclohexane ring. Non-limiting examples of heteroaryls include pyridyl, pyrazinyl, furanyl, thienyl, pyrimidinyl, pyridine (including N-substituted pyridines), isoxazolyl, isothiazolyl, oxazolyl, oxadiazolyl, thiazolyl, pyrazonyl, furyl, pyrrolyl, triazolyl, 1,2,4-thiadiazolyl, pyrazinyl, pyridazinyl, indolyl, quinoxalinyl, phthalazinyl, oxindolyl, imidazo[1,2-a]pyridinyl, imidazo[2,1-b]thiazolyl, and alike. Heteroaryl or heteroaromatic groups described herein may be optionally substituted with one or more substituents groups, which are selected independently unless otherwise indicated. Suitable substituent groups for the heteroaryl or heteroaromatic groups are further described herein.

The terms "heterocyclyl", "heterocyclic" or "heteroalicyclic" may be used interchangeably herein, to refer to a non-aromatic saturated or partially saturated monocyclic or multicyclic ring system containing 3 to 11 ring atoms, wherein from 1 to 4 of the ring atoms are independently O, S, or N and the remainder of the ring atoms are carbon atoms. In one embodiment, a heterocyclic group is monocyclic and has 6 ring atoms, "6-membered heterocyclic ring". In another embodiment, a heterocyclic group is monocyclic and has 6 ring atoms with either 1 or 2 ring atoms being a heteroatom, "6-membered heterocyclic ring containing 1 or 2 heteroatoms". In another embodiment, a heterocyclic group is monocyclic and has either 4 or 5 ring atoms, "4- or 5-membered heterocyclic ring". In another embodiment, a heterocyclic group has 7, 8 or 9 ring atoms, "7-, 8- or 9-membered heterocyclic ring". In another embodiment, a heterocyclic group is bicyclic. A heterocyclic group can be joined to the rest of the molecule via a ring carbon or ring nitrogen atom. The nitrogen or sulphur atom of the heterocyclyl can be optionally oxidized to the corresponding N-oxide, S-oxide or S,S-dioxide. Non-limiting examples of the monocyclic heterocyclic rings include oxetanyl, piperidyl, pyrrolidinyl, piperazinyl, morpholinyl, thiomorpholinyl, thiazolidinyl, dihydropyranyl, pyran, 1,4-dioxanyl, tetrahydrofuranyl, tetrahydrothiophenyl, delta-lactam, delta-lactone and the like. Heterocyclic groups described herein may be optionally substituted with one or more substituents groups, which are selected independently unless otherwise indicated. Suitable substituent groups for the heterocyclic groups are further described herein. Heterocyclic groups may be unsubstituted or substituted by the same groups suitable for alkyl, aryl or heteroaryl. In one embodiment a heterocyclic ring contains 6 atoms and is substituted with 1 to 4 groups as defined herein, "6-membered heterocyclic ring substituted with one to four groups". In addition, ring nitrogen atoms may be optionally substituted, when specified, by groups suitable for an amine, e.g., alkyl, acyl, carbamoyl, sulfonyl substituents, etc., and ring S atoms may be optionally substituted by 1 or 2 oxo groups (i.e., $S(O)_q$, where q is 0, 1 or 2). In one embodiment a 4 or 5 membered heterocyclic ring is optionally substituted, as given above, "optionally substituted 4- or 5-membered heterocyclic ring". In another embodiment, a 7, 8- or 9-membered heterocyclic ring is optionally substituted, as given above, "optionally substituted 7-, 8- or 9-membered heterocyclic ring".

Aryl, heteroaryl and heterocyclic moieties described herein as optionally substituted ("optionally substituted") may be substituted by one or more substituent groups, which are selected independently unless otherwise indicated. Aryl, heteroaryl and heterocyclic moieties described herein as substituted ("substituted") are substituted by one or more substituent groups, which are selected independently unless otherwise indicated. Optionally substituted aryl, heteroaryl or heterocyclic groups typically contain from 1 to 5 optional substituents, sometimes 1 to 4 optional substituents, preferably 1 to 3 optional substituents, or more preferably 1-2 optional substituents. Substituted aryl, heteroaryl or heterocyclic groups contain at least one substituent as described herein and may optionally contain up to 5 total substituents each independently selected.

Substituent groups suitable for aryl, heteroaryl and heterocyclic rings include, but are not limited to: (C1-C8)alkyl, (C2-C8)alkenyl, (C2-C8)alkynyl, (C3-C8)cycloalkyl, 3-12 membered heterocyclyl, (C6-C12)aryl, 5-12 membered heteroaryl, halo, =O (oxo), =S (thiono), =N—CN, =N—OR$^X$, =NR$^X$, —CN, —C(O)R$^X$, —CO$_2$R$^X$, —C(O)NR$^X$R$^Y$, —SR$^X$, —SOR$^X$, —SO$_2$R$^X$, —SO2NR$^X$R$^Y$, —NO$_2$, —NR$^X$R$^Y$, —NR$^X$C(O)R$^y$, —NR$^X$C(O)NR$^X$R$^Y$, —NR$^X$C(O)OR$^X$, —NR$^X$SO$_2$R$^Y$, —NR$^X$SO$_2$NR$^X$R$^Y$, —OR$^X$, —OC(O)R$^X$ and —OC(O)NR$^X$R$^Y$; where in each R$^X$ and R$^Y$ is independently hydrogen, (C1-C6)alkyl, (C2-C6)alkenyl, (C2-C6)alkynyl, (C3-C6)cycloalkyl, 3-12 membered heterocyclyl, (C6-C12)aryl, or 5-12 membered heteroaryl, or R$^X$ and R$^Y$ may be taken together with the nitrogen atom to which they are attached to form a 3-12 membered heterocyclyl or 5-12 membered heteroaryl system, each optionally containing 0, 1 or 2 additional heteroatoms; each R$^X$ and R$^Y$ is optionally substituted with 1 to 3 substituents independently selected from the group consisting of halo, =O, —CN, —C(O)R', —CO$_2$R', —C(O)NR'$_2$, —SO$_2$R', —NR'$_2$, —OR', wherein each R' is independently hydrogen, (C1-C6)alkyl, (C3-C6)cycloalkyl, or 3-12 membered heterocyclyl. However, suitable substituent for "substituted alkyl" does not include hydrogen.

"Unsubstituted amino" refers to a group —NH$_2$. Where the amino is described as substituted or optionally substituted, the term includes groups of the form —NR$^X$R$^Y$, where each R$^X$ and R$^Y$ is independently selected from hydrogen, (C1-C8)alkyl, (C3-C9)cycloalkyl, alkynyl, heterocyclyl, acyl, aryl, heteroaryl, thioacyl, cycloalkylalkyl, arylalkyl, or heteroalkylalkyl, in each case having the specified number of atoms and optionally substituted as described herein. Typically, alkyl substituents on amines contain 1 to 8 carbon atoms, preferably 1 to 6 carbon atoms, or more preferably 1 to 4 carbon atoms. The term also includes forms wherein R$^X$ and R$^Y$ are taken together with the nitrogen to which they are attached to form a 3-12 membered heterocyclyl or 5-12 membered heteroaryl ring, each of which may be optionally substituted as described herein for heterocyclyl or heteroaryl rings and which may contain 1 to 3 additional heteroatoms selected from N, O, and S as ring members, provided that such rings do not contain contiguous oxygen atoms or contiguous sulphur atoms. The term, as described above, extends to the amino residue of another functional group (for example, —C(O)NR$^X$R$^Y$, —S(O)$_2$NR$^X$R$^Y$, and alike). In one embodiment, R$^X$ and R$^Y$ of —NR$^X$R$^Y$; of —C(O)NR$^X$R$^Y$, may be taken together with the nitrogen to which they are attached to form a ring (a 3-12 membered heterocyclyl or 5-12 membered heteroaryl ring, each of which may be optionally substituted as described herein for heterocyclyl or heteroaryl rings and which may contain 1 to 3 additional heteroatoms selected from N, O, and S as ring members, provided that such rings do not contain contiguous oxygen atoms or contiguous sulphur atoms). In another embodiment, R$^X$ and R$^Y$ of —NR$^X$R$^Y$; of —S(O)$_2$NR$^X$R$^Y$, may be taken together with the nitrogen to which they are attached to form a ring (a 3-12 membered heterocyclyl or 5-12 membered heteroaryl ring, each of which may be optionally substituted as described herein for heterocyclyl or heteroaryl rings and which may contain 1 to 3 additional heteroatoms selected from N, O, and S as ring members, provided that such rings do not contain contiguous oxygen atoms or contiguous sulphur atoms).

Two adjacent substituents on a ring may be taken together, with the atoms to which they are attached, to form a ring. The term "together with the carbon atoms to which they are attached may form a ring" is defined herein to mean two adjacent residues residing on a ring may be combined together with the carbon atoms to which they are attached to form a 4-6 membered heterocyclyl, a 4-6 membered carbocyclyl, or a 4-6membered heteroaryl ring, each of which may be optionally substituted as described herein for heterocyclyl or heteroaryl rings. Thus formed heterocyclyl and heretoaryl rings may contain 1 to 3 additional heteroatoms selected from N, O, and S as ring members, (provided that such rings do not contain contiguous oxygen atoms or contiguous sulphur atoms). Representative examples derived from a phenyl moiety include, but are not limited to, benzofuranyl, benzothiophenyl, indolyl, benzimidazolyl, indazolyl, benzotrizolyl, indazolyl, quinolinyl, isoquinolinyl, cinnolinyl, azaquinazoline, quinoxalinyl, 2,3-dihydro-1H-indenyl, phthalanyl, 2,3-dihydrobenzofuryl, benzodioxoyl, benzodioxanyl, and the like. Representative examples thus formed heterocyclyl rings include, but are not limited to:

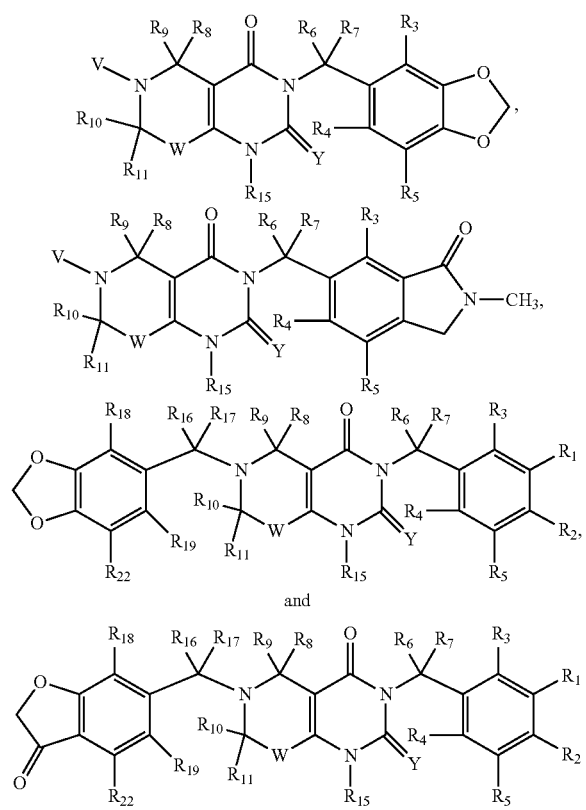

and alike. Representative examples thus formed carbocyclyl rings include, but are not limited to:

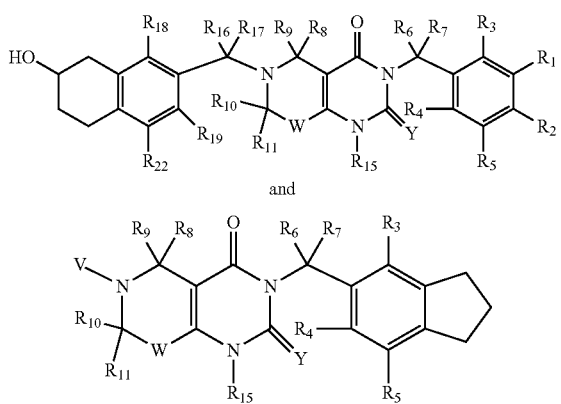

and alike.

Two substituents bound to a common nitrogen atom may be taken together, with the nitrogen to which they are attached, to form a ring. The term "together with the nitrogen atom to which they are attached may form a ring" is defined herein to mean two residues residing on a nitrogen atom may be combined together to form a 3-12-membered heterocyclyl, a 3-7-membered carbocyclyl, or a 5-12-membered heteroaryl ring, each of which may be optionally substituted as described herein for heterocyclyl or heteroaryl rings. Thus formed heterocyclyl and heteroaryl rings may contain 1 to 3 additional heteroatoms selected from N, O, and S as ring members, (provided that such rings do not contain contiguous oxygen atoms or contiguous sulphur atoms). Non-limiting examples derived from a nitrogen atom include the following moieties: azetidinyl, pyrrolidinyl, piperidinyl, morpholinyl, 1,4-azathianyl, 1,3,4-triazolyl, tetrazolyl, imidazolyl and alike.

The term "substituted" means that one or more hydrogen atoms of the designated are replaced with a selection from the indicated group, provided that the atoms' normal valencies under the existing circumstances are not exceeded, and that the substitution results in a stable compound. By "stable compound" or "stable structure" is meant a compound that is sufficiently robust to survive isolation to a useful degree of purity from a reaction mixture, and formulation into an efficacious therapeutic agent.

When any substituent or variable occurs more than one time in any constituent or the compound of Formula (I), its definition on each occurrence is independent of its definition at every other occurrence, unless otherwise indicated.

The term "in purified form" as used herein, refers to the physical state of a compound after the compound is isolated from a synthetic process (e.g., from a reaction mixture), a natural source, or a combination thereof. The term "in purified form" also refers to the physical state of a compound after the compound is obtained from a purification process or processes described herein or well-known to the skilled artisan (e.g., chromatography, recrystallization and the like).

It should be noted that any carbon as well as heteroatom with unsatisfied valences in the text, schemes, examples and tables herein is assumed to have the sufficient number of hydrogen atom(s) to satisfy the valences.

One or more compounds of the invention may exist in unsolvated as well as solvated forms with pharmaceutically acceptable solvents such as water, ethanol, and the like, and it is intended that the invention embrace both solvated and unsolvated forms.

The compounds of Formula (I) may contain one or more stereogenic centers and can thus occur as racemates, racemic mixtures, single enantiomers, diastereomeric mixtures and individual disatereomers. Each such asymmetric center will independently produce two optical isomers and it is intended that all of the possible optical isomers and diastereomers in mixtures and as pure or partially purified compounds are included within the ambit of this invention.

As used herein, the term "composition" is intended to encompass a product comprising the specified ingredients in the specified amounts, as well as any product which results, directly or indirectly, from combination of the specified ingredients in the specified amounts.

In the compounds of generic Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula (I). Enriching in a particular isotope may provide an advantageous characteristic(s), for example enriching for deuterium may afford certain therapeutic advantages, such as increasing in vivo half-life or reducing dosages. In addition, isotopic enrichment may also enrich a compound's usefulness in the characterization of biological samples. Compounds enriched in a specific isotope may be prepared via synthetic methods described herein and methods known to those skilled in the art by using reagents and starting material enriched with the specific isotope.

Prodrugs of the compounds of the invention are contemplated herein. The term "prodrug", as employed herein, denotes a compound which upon administration to a subject, undergoes chemical conversion by metabolic or chemical processes to yield a compound of Formula (I). Prodrugs may have beneficial properties, such as but not limited to, the enhancement of absorption and/or oral bioavailability.

The compounds of Formula (I) may in some cases form salts which are also with the scope of this invention. Reference to a compound of the formula (I) herein is understood to include reference to salts thereof, unless otherwise noted. The term "salt(s)" as used herein denotes acidic and/or basic salts formed with inorganic and/or organic acids and bases. Zwitterionic (internal or inner salts) are included within the term "salt(s)" as used herein (and may be formed, for example, where the R substituents comprise an acid moiety such as a carboxyl group). Also included herein are quaternary salts ammonium salts such as alkylammonium salts. Pharmaceutically acceptable (i.e., non-toxic, physiologically acceptable) salts are preferred, although other salts are useful, for example, in isolation or purification steps which may be employed during preparation. Salts of the compounds of the Formula (I) may be formed, for example, by reacting a compound of Formula (I) by reacting a compound of Formula (I) with an equivalent amount of an acid or base in a medium such as one the allows for the precipitation of the salt (example, ether) or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobrom ides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates), and the like. Additionally, acids which are generally considered suitable for the formation of pharmaceutically useful salts from basic pharmaceutical compounds are discussed, for example by P. Stahl et al, Camille G. (eds.) Handbook of Pharmaceutical Salts. Properties, Selection and Use. (2002) Zurich: Wiley-VCH. This disclosure is incorporated herein by reference.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

The present invention further includes compounds of Formula (I) in all their isolated forms.

Compounds of the Invention

In one aspect, the invention provides a compound of Formula (I):

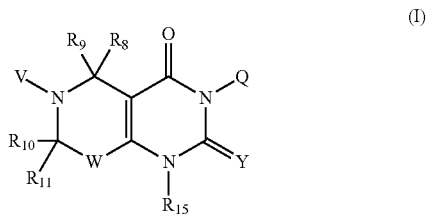

(I)

wherein

Q is independently selected from the group consisting of heteroaryl,

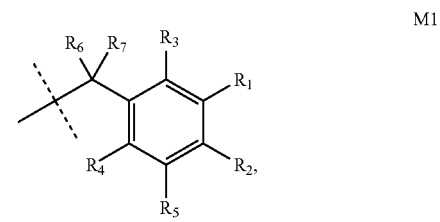

M1

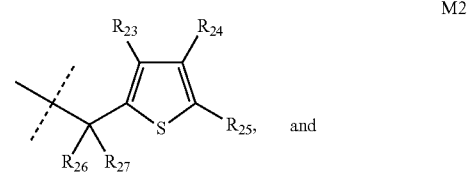

M2

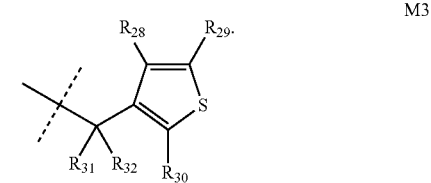

M3

V is independently selected from the group consisting of:

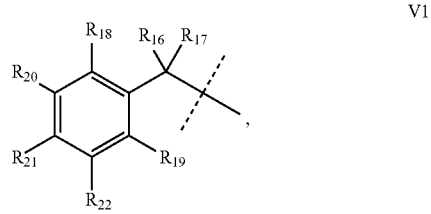

V1

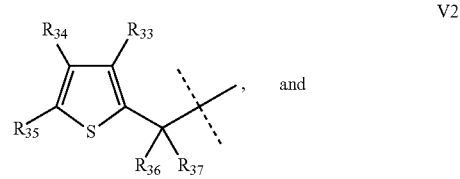

V2

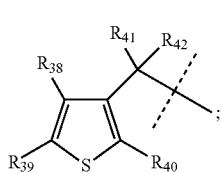

W is absent or —C($R_{12}R_{13}$)—; Y is independently selected from the group consisting of oxygen, sulphur, and =$NR_{14}$; $R_1$, $R_2$, $R_3$, $R_4$, and $R_5$ are independently selected from the group consisting of hydrogen, halogen, —CN, —S(O)$_2R_{43}$, —NO$_2$, —$NR_{44}R_{45}$, —OH, —SH, —$SR_{46}$, (C1-C3)haloalkyloxy, (C1-C4)alkoxy, (C1-C6)alkyl, (C3-C6)cycloalkyl, (C2-C6)alkynyl, (C2-C6)alkenyl and (C1-C6)haloalkyl; or alternatively, $R_1$ and $R_2$ may be taken together with the carbon atoms to which they are attached to form a ring; $R_{23}$, $R_{24}$, $R_{25}$, $R_{28}$, $R_{29}$ and $R_{30}$ are independently selected from the group consisting of hydrogen, halogen, —CN, —S(O)$_2R_{43}$, —NO$_2$, —$NR_{44}R_{45}$, —OH, —SH, —$SR_{46}$, (C1-C3)haloalkyloxy, (C1-C4)alkoxy, (C1-C6)alkyl, (C3-C6)cycloalkyl, (C2-C6)alkynyl, (C2-C6)alkenyl and (C1-C6)haloalkyl; or alternatively, $R_{24}$ and $R_{25}$ may be taken together with the carbon atoms to which they are attached to form a ring; $R_{28}$ and $R_{29}$ may be taken together with the carbon atoms to which they are attached to form a ring;

$R_6$, $R_7$, $R_8$, $R_9$, $R_{10}$, $R_{11}$, $R_{12}$, $R_{13}$, $R_{16}$, $R_{17}$, $R_{26}$, $R_{27}$, $R_{31}$, $R_{32}$, $R_{36}$, $R_{37}$, $R_{41}$, and $R_{42}$ are each independently selected from the group consisting of hydrogen, halogen, —CN, —S(O)$_2R_{43}$, —NO$_2$, —NRR, —OH, —SH, —$SR_{46}$, (C1-C3)haloalkyloxy, (C1-C4)alkoxy, (C1-C6)alkyl, (C3-C6)cycloalkyl, (C2-C6)alkynyl, (C2-C6)alkenyl and (C1-C6)haloalkyl; or alternatively, $R_6$ and $R_7$ together with the carbon atom to which they are attached may form a 3-membered carbocyclic ring or a carbonyl moiety; $R_8$ and $R_9$ together with the carbon atom to which they are attached may form a 3-membered carbocyclic ring or a carbonyl moiety; $R_{10}$ and $R_{11}$ together with the carbon atom to which they are attached may form a 3-membered carbocyclic ring or a carbonyl moiety; $R_{12}$ and $R_{13}$ together with the carbon atom to which they are attached may form a 3-membered carbocyclic ring or a carbonyl moiety; $R_{16}$ and $R_{17}$ together with the carbon atom to which they are attached may form a 3-membered carbocyclic ring or a carbonyl moiety; $R_{26}$ and $R_{27}$ together with the carbon atom to which they are attached may form a 3-membered carbocyclic ring or a carbonyl moiety; $R_{31}$ and $R_{32}$ together with the carbon atom to which they are attached may form a 3-membered carbocyclic ring or a carbonyl moiety; $R_{36}$ and $R_{37}$ together with the carbon atom to which they are attached may form a 3-membered carbocyclic ring or a carbonyl moiety; $R_{41}$ and $R_{42}$ together with the carbon atom to which they are attached may form a 3-membered carbocyclic ring or a carbonyl moiety; $R_{14}$ and $R_{15}$ are independently selected from the group consisting of hydrogen, halogen, —CN, —S(O)$_2R_{43}$, —NO$_2$, —$NR_{44}R_{45}$, —OH, —SH, —$SR_{46}$, —S(O)$_2R_{43}$, (C1-C3)haloalkyloxy, (C1-C4)alkoxy, (C1-C6)alkyl, (C3-C6)cycloalkyl, (C2-C6)alkynyl, (C2-C6)alkenyl and (C1-C6)haloalkyl, —C(NH)NH$_2$, —C(O)$R_{43}$, —C(O)$OR_{46}$; $R_{18}$, $R_{19}$, $R_{20}$, $R_{21}$, and $R_{22}$ are independently selected from the group consisting of the following: hydrogen, halogen, (C1-C6)alkyl, (C3-C9)cycloalkyl, (C3-C9)cycloalkyl(C1-C6)alkyl, (C1-C6)haloalkyl, —OH, —SH, (C1-C6)alkoxy, —$NR_{44}R_{45}$, (C3-C9)cycloalkyl(C2-C6)alkynyl, (C4-C8)cycloalkenyl, (C4-C8)cycloalkenyl(C1-C6)alkyl, aryl, heteroaryl, heterocyclyl, —CN, —NO$_2$, —$SR_{46}$, —C(O)OH, —C(O)$OR_{46}$, —OC(O)$OR_{46}$, (C2-C6)alkynyl, (C2-C8)alkenyl, (C1-C6)haloalkyoxy, —S(O)$_2OR_{40}$, —SO$_2NR_{44}R_{45}$, —S(O)$_2R_{43}$, —$NR_{47}$S(O)$_2R_{43}$, —C(O)$NR_{44}R_{45}$, —C(O)$R_{43}$, and —$NR_{47}$C(O)$R_{43}$; or alternatively, $R_{20}$ and $R_{21}$ may be taken together with the carbon atoms to which they are attached to form a ring; $R_{33}$, $R_{34}$, $R_{35}$, $R_{38}$, $R_{39}$ and $R_{40}$ are independently selected from the group consisting of the following: hydrogen, halogen, (C1-C6)alkyl, (C3-C9)cycloalkyl, (C3-C9)cycloalkyl(C1-C6)alkyl, (C1-C6)haloalkyl, —OH, —SH, (C1-C6)alkoxy, —$NR_{44}R_{45}$, (C3-C9)cycloalkyl(C2-C6)alkynyl, (C4-C8)cycloalkenyl, (C4-C8)cycloalkenyl(C1-C6)alkyl, aryl, heteroaryl, heterocyclyl, —CN, —NO$_2$, —$SR_{46}$, —C(O)OH, —C(O)$OR_{46}$, —OC(O)$OR_{46}$, (C2-C6)alkynyl, (C2-C8)alkenyl, (C1-C6)haloalkyoxy, —S(O)$_2OR_{46}$, —SO$_2NR_{44}R_{45}$, —S(O)$_2R_{43}$, —$NR_{47}$S(O)$_2R_{43}$, —C(O)$NR_{44}R_{45}$, —C(O)$R_{43}$, and —$NR_{47}$C(O)$R_{43}$; or alternatively, $R_{34}$ and $R_{35}$ may be taken together with the carbon atoms to which they are attached to form a ring; $R_{38}$ and $R_{39}$ may be taken together with the carbon atoms to which they are attached to form a ring; $R_{43}$ is independently selected from the group consisting of hydrogen, (C1-C6)alkyl, (C3-C9)cycloalkyl, (C1-C6)haloalkyl, (C2-C6)alkynyl, (C2-C8)alkenyl, (C1-C6)haloalkyoxy, aryl, heteroaryl, heterocyclyl and —$NR_{44}R_{45}$; $R_{44}$, $R_{45}$ and $R_{47}$ are independently selected from the group consisting of hydrogen, (C1-C6)alkyl, (C3-C9)cycloalkyl, (C1-C6)haloalkyl, (C2-C6)alkynyl, (C2-C8)alkenyl, (C1-C6)haloalkyoxy, aryl, heteroary and heterocyclyl; or alternatively, $R_{44}$ and $R_{45}$ together with the nitrogen atom to which they are attached may form a ring; $R_{46}$ is independently selected from the group consisting of hydrogen, (C1-C6)alkyl, (C3-C9)cycloalkyl, (C1-C6)haloalkyl, (C2-C6)alkynyl, (C2-C8)alkenyl, (C1-C6)haloalkyoxy, aryl, heteroaryl and heterocyclyl; or a pharmaceutically acceptable salt thereof.

In frequent embodiments, of Formula (I), $R_3$, $R_4$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$ are hydrogen.

In frequent embodiments, of Formula (I), $R_{15}$ is —$CH_3$.

In frequent embodiments, of Formula (I), $R_{15}$ is —$CH_3$ and Y is oxygen.

In some embodiments, of Formula (I), $R_{15}$ is hydrogen, —$CH_2CH_3$ and —$CH(CH_3)_2$.

In some embodiments, of Formula (I), $R_2$ is —Cl, —Br or —$CF_3$.

In some embodiments of Formula (I), $R_2$ is —Cl and $R_3$, $R_4$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$ are hydrogen.

In some embodiments of Formula (I), $R_2$ is —Br and $R_3$, $R_4$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$ are hydrogen.

In some embodiments of Formula (I), $R_2$ is —$CF_3$ and $R_3$, $R_4$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$ are hydrogen.

In some embodiments of Formula (I), $R_{22}$ is (C2-C6)alkynyl.

In some embodiments of Formula (I), $R_{22}$ is (C2)alkynyl and $R_2$ is —$CF_3$.

In some embodiments of Formula (I), $R_{22}$ is (C2)alkynyl and $R_2$ is —Cl.

In some embodiments of Formula (I), $R_{22}$ is (C2)alkynyl and $R_2$ is —Br.

Dosage Forms and Regimens

Administration of compounds of the invention may be affected by any method that enables delivery of the compounds to the site of action. These methods include oral routes, intraduodenal routes, parenteral injection (including intravenous, subcutaneous, intramuscular, or infusion), topical and rectal administration.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dose. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention may be dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose may be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention. It is to be noted that dosage values may vary with the type and severity of the condition to be alleviated, and may include single or multiple doses. It is to be further understood that for any particular subject, specific dosage regimens should be adjusted over time according to the individual need and the professional judgement of the person administering or supervising the administration of the compositions, and that dosage ranges set forth herein are exemplary only and are not intended to limit the scope or practice of the claimed composition. For example, doses may be adjusted based on pharmacokinetic or pharmacodynamics parameters, which may include clinical effects such as toxic effects and/or laboratory values. Thus, the present invention encompasses intra-patient dose-escalation as determined by the skilled artisan. Determining appropriate dosages and regimens for administration of the chemotherapeutic agent are well-known in the relevant art and would be understood to be encompassed by the skilled artisan once provided the teachings disclosed herein.

The amount of the compound of the invention administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.1 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

Formulations and Routes of Administration

As used herein, a "pharmaceutically acceptable carrier" refers to a carrier or diluent that does not cause significant irritation to an organism and does not abrogate the biological activity and properties of the active compound.

The pharmaceutically acceptable carrier may comprise any conventional pharmaceutical carrier or excipient. The choice of carrier and/or excipient, will to a large extent, depend on factors such as the particular mode of administration, the effect of the excipient on solubility and stability, and the nature of the dosage form.

Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Examples without limitation, of excipients include calcium carbonate, calcium phosphate, various sugars and types of starch, cellulose derivatives, gelatin, vegetable oils and polyethylene glycols. Additionally, lubricating agents such as magnesium stearate, sodium lauryl sulfate and talc are often useful for tableting purposes. Solid compositions of a similar type may also be employed in soft and hard filled gelatin capsules. Non-limiting examples of material, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The pharmaceutical composition may, for example, be in a form suitable for oral administration as a tablet, capsule, pill, powder, sustained release formulation, solution, suspension or emulsion, for topical administration as an ointment or crease, or for rectal administration as a suppository.

Exemplary parenteral administration forms include solutions or suspensions of an active compound in a sterile aqueous solution, for example, aqueous propylene glycol or dextrose solutions. Such dosage forms may be suitably buffered, if desired.

The pharmaceutical composition may be in unit dosage forms suitable for single administration of precise amounts.

Pharmaceutical compositions suitable for the delivery of active agents and methods for their preparation will be readily apparent to those skilled in the art. Such compositions and methods for their preparation may be found, for example, in "Remington's Pharmaceutical Sciences", 19th Edition (Mack Publishing Company, 1995), the disclosure of which is incorporated herein by reference in its entirety.

Compounds of the invention may be administered orally. Oral administration may involve swallowing, so that the compound enters the gastrointestinal tract, buccal or sublingual administration may be employed by which the compounds enters the blood stream directly from the mouth.

Formulations suitable for oral administration include solid formulations such as tablets, capsules containing particulates, liquids, or powders. Lozenges (including liquid filled), chews, multi- and nano-particulates, gels solid solution, liposome, films, ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Compounds of the invention may also be used in fast-dissolving, fast-disintegrating dosage forms such as those described in Expert Opinion in Therapeutic Patents, 11 (6), 981-986 by Liang and Chen (2001), the disclosure of which is incorporated herein by reference in its entirety.

For tablet dosage forms, the active agent may make up from 1 wt % to 80 wt % of the dosage form, more typically from 5 wt % to 60 wt % of the dosage form. In addition to the active agent, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant may comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl, cellulose and hydroxypropyl methylcellulose. Tablets may also contain diluents, such as lactose, mannitol, xylitol, dextrose, sucrose, sorbitol, microcrystalline cellulose, starch, and dibasic calcium phosphate dehydrate.

Tablets may also optionally include surface active agents such as sodium lauryl sulfate and ploysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet.

Exemplary tablets may contain up to about 80 wt % active agents for about 10 wt % to about 90 wt % binder, from about 0 wt % to about 85 wt % diluent, from about 2 wt % to about 10 wt % disintegrant, and from about 0.25 wt % to about 10 wt % lubricant.

The formulation of tablets is discussed in detail in "pharmaceutical Dosage Forms: Tablets, Vol. 1", by H. Lieberman and L. Lachman, Marcel Dekker, N.Y., N.Y., 1980 (ISBN 0-8247-6918-X), the disclosure of which is incorporated herein by reference in its entirety.

Suitable modified release formulations are described in U.S. Pat. No. 6,106,864. Details of other suitable release technologies such as high energy dispersions and osmotic and coated particles may be found in Verma et al, Pharmaceutical Technology On-line 25(2), 1-14 (2001). This disclosure of this reference is incorporated herein by reference in its entirety.

It is understood that compounds of Formula (I) can be formulated as a di-salt.

Parenteral Administration

Compounds of the invention may also be administered directly into the blood stream, into muscle, or into an internal organ. Suitable means for parenteral administration including intravenous, intraarterial, intraperitoneal, intrathecal, intraventricular, intraurethral, intracranial, intramuscular and subcutaneous. Suitable devices for parenteral administration include needle injectors, needle-free injectors and infusion techniques.

Parenteral formulations are typically aqueous solutions which may contain excipients such as salts, carbohydrates and buffering agents (preferably to a pH of 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of the invention used in the preparation of parenteral solutions may potentially be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may potentially be formulated as a solid, semi-solid, or thixotropic liquid for administration as an implanted depot providing modified release of the active compound. Examples of such formulations include drug-coated stents and PGLA microspheres.

The compounds of the invention may also potentially be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers bandages and microemulsions.

Dosage

The amount of the active compound administered will be dependent on the subject being treated, the severity of the disorder or condition, the rate of administration, the disposition of the compound and the discretion of the prescribing physician. However, the effective dose is typically in the range of about 0.001 to about 100 mg per kg body weight per day, preferably 0.01 to about 35 mg/kg/day, in a single or divided doses. For a human, this would amount to about 0.07 to about 700 mg/day, preferably about 0.7 to about 2500 mg/day. In some instances, dosage levels below the lower limit of the aforesaid range may be more than adequate, while in other cases still larger doses may be used without causing any harmful side effect, with such larger doses typically divided into several smaller doses for administration throughout the day.

Combination Therapy

As used herein, the term "combination therapy" refers to the administration of a compound of the invention together with at least one additional pharmaceutical or medicinal agent (e.g., an anti-cancer agent), either sequentially or simultaneously.

As noted above, the compounds of the invention may potentially be used in combination with one or more additional anti-cancer agents, which are described below. When a combination therapy is used, the one or more additional anti-cancer agent may be administered sequentially or simultaneously with the compound of the invention. In one embodiment, the additional anti-cancer agent is administered to a mammal (subject, patient) prior to administration of the compound of the invention. In another embodiment, the additional anti-cancer agent is administered to the mammal after administration of the compound of the invention. In another embodiment, the additional anti-cancer agent is administered to the mammal simultaneously with the administration of the compound of the invention.

The invention also relates to a pharmaceutical composition for the treatment of abnormal cell growth in a mammal, including a human, which comprises an amount of a compound of the invention, as defined herein, in combination with one or more (preferably one to three) anti-cancer agents selected from a group consisting of anti-angiogenesis agents and signal transduction inhibitors and a pharmaceutically acceptable carrier, wherein the amounts of the active agent and the combination anti-cancer agents when taken as a whole is therapeutically effective for treating said abnormal cell growth.

In one embodiment of the present invention the anti-cancer agent used in conjunction with a compound of the invention and pharmaceutical compositions described herein is an anti-angiogenesis agent (e.g., an agent that stops tumors from developing new blood vessels). Examples of anti-angiogenesis agents include for example VEGF inhibitors, VEGFR inhibitors, TIE-2 inhibitors, PDGFR inhibitors, angiopoetin inhibitors, PKCbeta inhibitors, COX-2 inhibitors, integrins, MMP-2 (matrix-metalloproteinase 2) inhibitors, and MMP-9 (matrix-metalloproteinase 9) inhibitors.

Preferred anti-angiogenesis agents include sunitinib (Sutent™) bevacizumab (Avastin™) axitinib (AG 13736), SU 14813 (Pfizer), and AG 13958 (Pfizer).

Additional anti-angiogenesis agents include vatalanib (CGP 79787), Sorafenib (Nexavar™), pegaptanib octasodium (Macugen™), vandetanib (Zactima™), PF-0337210 (Pfizer), SU 14843 (Pfizer), AZD 2171 (AstraZeneca), ranibizumab (Lucentis™), Neovastat™) (AE 941), tetrathiomolyb-data (Coprexa™), AMG 706 (Amgen), VEGF Trap (AVE 0005), CEP 7055 (Sanofi-Aventis), XL 880 (Exelixis), telatinib (BAY 57-9352), and CP-868,596 (Pfizer).

Other anti-angiogenesis agents include enzastaurin (LY 317615), midostaurin (CGP 41251), perifosine (KRX 0401), teprenone (Selbex™) and UCN 01 (Kyowa Hakko).

Other examples of anti-angiogenesis agents which may be used in conjuction with a compound of the invention and pharmaceutical compositions described herein include celecoxib (Celebrex™), parecoxib (Dynastat™), deracoxib (SC 59046), lumiracoxib (Preige™), valdecoxib (Bextra™), rofecoxib (Vioxx™), iguratimod (Careram™), IP 751 (Invedus), SC-58125 (Pharmacia) and etoricoxib (Arcoxia™).

Other anti-angiogenesis agents include exisulind (Aptosyn™), salsalate (Amigesic™), diflunisal (Dolobid™), ibuprofen (Motrin™), ketoprofen (Orudis™) nabumetone (Relafen™), piroxicam (Feldene™), naproxen (Aleve™, Naprosyn™) diclofenac (Voltarn™), indomethacin (Indocin™), sulindac (Clinoril™), tolmetin (Tolectin™), etodolac (Lodine™), ketorolac (Toradol™), and oxaprozin (DayPro™).

Other anti-angiogenesis agents include ABT 510 (abbott), apratastat (TMI 005), AZD 8955 (AstraZeneca), incyclinide (Metastat™), and PCK 3145 (Procyon).

Other anti-angiogenesis agents include acitretin (Neotigason™), plitidepsin (Aplidine™), cilengtide (EMD 121974), combretastatin A4 (CA4P), fenretinide (4 HPR), halofuginone (Tempostatin™), Panzem™, rebimastat (BMS 275291), catumaxomab, (Removab™), lenalidomide (Revlimid™), squalamine (EVIZON™), thalidomide (Thalomid™), Ukrain™ (NSC 631570), Vitaxin™ (MEDI 522), and zoledronic acid (Zomata™).

In another embodiment the anti-cancer agent is a so called signal transduction inhibitor (e.g., inhibiting the means by which regulatory molecules that govern the fundamental processes of cell growth, differentiation, and survival communicated within the cell). Signal transduction inhibitors include small molecules, antibodies, and antisense molecules. Signal transduction inhibitors include for example kinase inhibitors (e.g., tyrosine kinase inhibitors or serine/threonine kinase inhibitors) and cell cycle inhibitors. More specifically signal transduction inhibitors include, for example, farnesyl protein transferase inhibitors, EgF inhibitors, ErbB-1 (EGFR) inhibitors, ErbB-2 inhibitors, pan-erb inhibitors, IGF1R inhibitors, MEK (1,2) inhibitors, c-Kit inhibitors, FLT-3 inhibitors, K-Ras inhibitors, PI3 kinase inhibitors, JAK inhibitors, STAT inhibitors, Raf kinase inhibitors, Akt inhibitors, mTOR inhibitors, P70S6 kinase inhibitors, inhibitors of the WNT pathway and so called multi-targeted kinase inhibitors.

Preferred signal transduction inhibitors include gefitinib (Iressa™), cetuximab (Erbitux™), erlotinib (Tarceva™), trastuzmab (Herceptin™), sunitinib (Sutent™) imatinib (Gleevec™), Trametinib™ (GSK1120212) and Cobimetinib™ (XL518).

Additional examples of signal transduction inhibitors which may be used in conjunction with a compound of the invention and pharmaceutical compositions described herein include BMS 214662, lonafarnib (Sarasar™), pelitrexol (AG 2037), matuzumab (EMD 7200), nimotuzumab (TheraCIM h-R3™), panitumumab (Vectibix™), Vandetanib (Zactima™), pazopanib (SB 786034), BIBW 2992 (Boehringer Ingelheim), and Cervene™ (TP 38).

Other examples of signal transduction inhibitors include Canertinib (CI 1033), pertuzumab (Omnitarg™), Lapatinib (Tycerb™), pelitinib (EKB 569), miltefosine (Miltefosin™), BMS 599626, Lapuleucel-T (Neuvenge™), NeuVax™), Osidem™ (IDM 1), mubritinib (TAK-165), Panitumumab (Vectibix™), lapatinib (Tycerb™), pelitinib (EKB 569), and pertuzumab (Omnitarg™).

Other examples of signal transduction inhibitors include ARRY 142886, everolimus (Certican™), zotarolimus (Endeavor™), temsirolimus (Torisel™), and VX 680 (Vertex).

This invention contemplates the use of a compound of the invention together with antineoplastic agents. Antineoplastic agents include, but are not limited to, hormonal, antiestrogen therapeutic agents, histone deacetylase (HDAC) inhibitors, gene silencing agents or gene activating agents, ribonucleases, proteosomics, Topoisomerase I inhibitors, Camptothecin derivatives, Topoisomerase II inhibitors, alkylating agents, antimetabolites, poly(ADP-ribose), polymerase-1 (PARP-1) inhibitors microtubulin inhibitors, antibiotics, spindle inhibitors, platinum-coordinated compounds, gene therapeutic agents, antisense oligonucleotides, vascular targeting agents (VTAs) and statins.

Examples of antineoplastic agents used in combination therapy with a compound of the invention, include, but are not limited to, glucocorticoids, such as dexamethasone, prednisone, prednisolone, methylprednisolone, hydrocortisone, and progestins such as medroxyprogesterone, megestrol acetate (Megace), mifepristone (RU-486) selective estrogen receptor modulators (SERMs, such as tamoxifen, raloxifene, lasofoxifene, afimoxifene, arzoxifene, bazedoxifene, fispemifene, ormeloxifene, ospemifene, tesmilifene, toremifene, trilostance and CHF 4227 (Cheisi), selective estrogen-receptor downregulators (SERDs, such as fulvestrant), exemestane (Aromasin™), anastrozole (Arimidex™), atamestane, fadrozole, letrozole (Femara), gonadotropin-releasing hormone (GnRH, also commonly referred to as luteinizing hormone-releasing hormone [LHRH]) agonists such as buserelin (Suprefact), goserelin (Zoladex), leuprorelin (Lupron), and triptorelin (Trelstar), abarelix (Plenaxis), bicalutamide (Casodex), cyproterone, flutamide (Eulexin), megestrol, nilutamide (Nilandron), and osaterone, dutasteride, epristeride, finasteride, abarelix, goserelin, leuprorelin, triptorelin, bicalutamide, tamoxifen, exemestane, anastrozole, fadrozole, fromestane, letrozole, and combinations thereof.

Other example of antineoplastic agents used in combination with a compound of the invention include, but are not limited to, suberolanilide hydroxamic acid (SAHA™, Merck), depsipeptide (FR901228), G2M-777, MS-275, pivaloyloxymethyl butyrate and PXD-101/Onconase™ (ranpimase), PS-341, Valcade™ (bortezomib), 9-aminocamptothecin, belotecan, BN-80915, camptothecin, diflomotecan, edotecarin, exatecan, gimatecan, 10-hydroxycamptothecin, irinotecan HCl (Camptosar™) lurtotecan, Orathecin™ (rubitecan, Supergen™), SN-38, topotecan, camptothecin, 10-hydroxycamptothecin, 9-aminocamptothecin, irinotecan, aclarubicin, adriamycin, amonafide, amrubicin, annamycin, daunorubicin, doxorubicin, elsamitrucin, epirubicin, etoposide, idarubicin, galarubicin, hydroxycarbamide, nemorubicin, novantrone (mitoxantrone), pirarubicin, pixantrone, procarbazine, rebeccamycin, sobuzoxane, tafluposide, valrubicin, Zinecard™ (dexrazoxane), nitrogen mustard N-oxide, cyclophosphamide, AMD-473, altretamine, Ap-5280, apaziquone, brostallicin, bendamustine, busulfan, carboquone, carmustine, chlorambucil, dacarbazine, estramustine, fotemustine, glufosfamide, ifosfamide, KW-2170, lomustine, mafosfamide, mechlorethamine, melphalan, mitobronitol, mitolactol, mitomycin C, mitoxatrone, nimustine, ranimustine, temozolomide, thiotepa, and platinum-coordinated alkylating agents such as cisplatin. Paraplatin (carboplatin), eptaplatin, lobaplatin, nedaplatin, Eloxatin™ (oxaliplatin), streptozocin, satrplatin, and combinations thereof.

The invention also contemplates the use of a compound of the invention together with dihydrofolate reductase inhibitors (for example methotrexate and NeuTrexin™ (trimetresate glucoronate)), purine antagonist (for example 6-mercaptopurine riboside, mercaptopurine, 6-thioguanine, cladribine, clofarabine (Clolar™), fludarabine, nelarabine, and raltitrexed), pyrimidine antagonists (for example, 5-fluorouracil (5-FU), Alimta™ (premetrexed disodium), capecitabine (Xeloda™), cytosine, Arabinoside, Gemzar™ (gemcitabine), Tegafur™ (UFT Orzel™ or UForal™ and including TS-1 combination of tegafur, gimestat and otostat), doxifluridine, carmofur, cytarabine (including ocfosfate, phosphate stearate, sustained release and liposomal forms), enocitabine, 5-azacitidine (Vidaza), decitabine, and ethynyl-cytidine) and other antimetabolites such as eflomithine, hydroxyurea, leucovorin, nolatrexed, triapine, trimetrexate, ABT-472, Ino-1001, KU-0687 and GPI 18180 and combinations thereof.

Additional examples of antineoplastic agents used in combination therapy with a compound of the invention, optionally with one or more other agents include, but are not limited to, Advexin™, Genasense (oblimersen, Genta), Combretastatin A4P (CA4P), Oxi4503, AVE-8062, ZD-6126, TZT 1027, atorvastatin (Lipitor™), pravastatin (Pravachol™), lovastatin (Mevacor™), simvastatin (Zocor™), fluvastatin (Lescol™), cerivastatin (Baycol™), rosuvastatin (Crestor™), niacin (Advicor™), caduet and combinations thereof.

Another embodiment of the present invention of particular interest relates to a method for the treatment of breast cancer in a human in need of such treatment, comprising administering to said human an amount of a compound of the invention, in combination with one or more (preferably one to three) anti-cancer agents selected from the group consisting of trastuzumab, tamoxifen, docetaxel, paclitaxel, capecitabine, gemcitabine, vinorelbine, exmestane, letrozole and anastrozole.

Therapeutic Methods and Uses

The invention further provides therapeutic methods and uses comprising administering a compound of the invention, or pharmaceutically acceptable salt thereof, alone or in combination with one or more other therapeutic agents or palliative agents.

In one aspect, the invention provides a method for the treatment of abnormal cell growth in a subject comprising administering to the subject a therapeutically effective amount of a compound of the invention, or a pharmaceutically acceptable salt thereof.

In another aspect, the invention provides a method for the treatment of abnormal cell growth in a subject comprising administering to the subject an amount of a compound of the invention, or a pharmaceutically acceptable salt thereof, in combination with an amount of an anti-tumor agent, which amounts are together effective in treating said abnormal growth. In some embodiments, the anti-tumor agent is selected from the group consisting of mitotic inhibitors, alkylating agents, antimetabolites, intercalating antibiotics, growth factor inhibitors, radiation, cell cycle inhibitors, enzymes, topoisomerase inhibitors, biological response modifiers, antibodies, cytotoxics, anti-hormones and anti-androgens.

In another aspect, the invention provides a method of inhibiting cancer cell proliferation in a subject, comprising administering to the subject a compound of the invention, or pharmaceutically acceptable salt thereof, in an amount effective to inhibit cell proliferation.

In another aspect, the invention provides a method of inhibiting cancer cell invasiveness in a subject, comprising administering to the subject a compound of the invention, or pharmaceutically acceptable salt thereof, in an amount effective to inhibit cell proliferation.

In another aspect, the invention provides a method of inducing apoptosis in cancer cells in a subject, comprising administering to the subject a compound of the invention, or pharmaceutically acceptable salt thereof, in an amount effective to inhibit cell proliferation.

In another aspect, the invention provides a method of inducing apoptosis in a subject, comprising administering to the subject a compound of the invention, or pharmaceutic acceptable salt thereof, in an amount effective to inhibit cell proliferation.

In frequent embodiments of the methods provided herein, the abnormal cell growth is cancer, wherein said cancer is selected from the group consisting of basal cell cancer, medulloblastoma cancer, liver cancer, rhabdomyosarcoma, lung cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In some embodiments, the cells are in a tissue or tumor, and the tissue or tumor may be in a subject, including a human.

Cancers treated using methods and compositions described herein are characterized by abnormal cell proliferation including, but not limited to, metastasis, pre-neoplastic hyperproliferation, cancer in situ, and neoplasms. Compounds of this invention can be for prophylaxis in addition to amelioration of signs and/or symptoms of cancer. Examples of cancers treated by the compounds of the present invention include, but are not limited to, breast cancer, CNS cancers, colon cancer, prostate cancer, leukemia, lung cancer and lymphoma.

Methods of Preparing the Compounds of Formula (I)

The compounds of this invention may be made by a variety of methods, including standard chemistry. Any previously defined variable will continue to have previously defined meaning unless otherwise noted. Illustrative general synthetic methods are set out below and then specific compounds of Formula (I) are prepared in the Examples.

Compounds of general Formula (I) may be prepared by methods known in the art of organic synthesis as set forth in part by the following synthetic schemes. In all the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) Protecting Groups in Organic Synthesis, John Wiley & Sons). Those skilled in the art will recognize whether a stereocenter exists in compounds of Formula (I). Accordingly, the present invention includes all possible stereoisomers and includes not only mixtures of stereoisomers (such as racemic compounds) but the individual stereoisomers. When a compound is desired as a single isomer it may be obtained by various methods of separation of the final product or key intermediate or alternatively may be made by a stereo specific synthesis using isomerically pure intermediates or methods to impart isomeric purity. These are known to those skilled in the art.

The following solvents, reagents, protecting groups, moieties, and other designations may be referred to by their abbreviations in parenthesis:
Me: methyl;
Et: ethyl;
Pr: propyl;
i-Pr: isopropyl;
Bu: butyl;
t-Bu: tert-butyl;
Ph: phenyl,
Ac: acetyl
AcOH: acetic acid
Aq.: aqueous
Conc.: concentrated
DMF: dimethylformamide
DMSO: dimethylsulfoxide
EtOAc: ethyl acetate
EtOH: ethyl alcohol
g: grams
h: hours
HPLC: high-performance liquid chromatography
LCMS: liquid chromatography mass spectrometry
MeOH: methyl alcohol
MS: mass spectrometry
NA: not applicable
Ret Time: retention time
RT or rt: room temperature
Satd or satd.: saturated
TFA: trifluoroacetic acid
THF: tetrahydrofuran Methods of Preparation Compounds of the invention may be prepared according to the general synthetic schemes and exemplary procedures provided herein and modifications thereof known to those of skill in the art. All documents cited are incorporated herein by reference in their entirety. Starting materials are commercially available or readily prepared by one of ordinary skill in the art.

A general synthetic scheme shown as Scheme 1, is a series of reactions that one skilled in the art may use to prepare compounds of the invention. Substituents X and Y denote various substituents that may be used for this reaction sequence and their positions on the molecule are not limited. Central to this chemical synthetic route is the use of isocyanates here shown as SI. In the case where A is a single chlorine atom and the remaining positions that may be substituted are hydrogen, the isocyanate required has the chemical formula of: $C_8H_6ClNO$. In addition, the last step is envisioned to allow for the attachment of various residues here identified by $R_{15}$. The reaction conditions shown allow for the attachment of various residues as $R_{15}$. This example is not to be limiting with regard to the number and type of substituents that may be used therein. Alternative reaction conditions, known to those skilled in the art, may be employed for the various transformations in Scheme 1. In order to provide additional clarity X may be $R_{21}$ and Y may be $R_2$ this is in no way meant to be limiting with the number and type of substituents that may be used.

Scheme 1

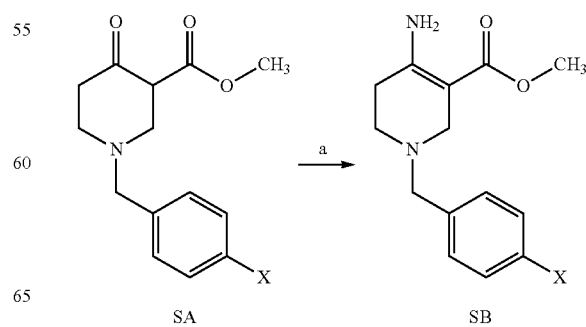

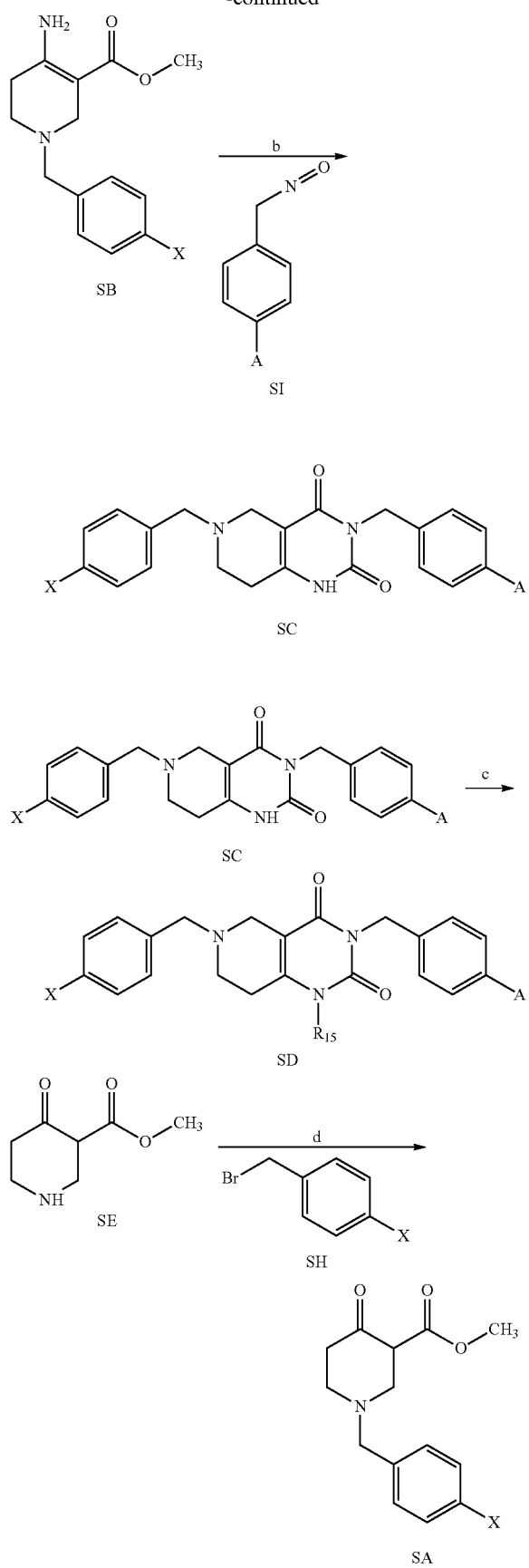

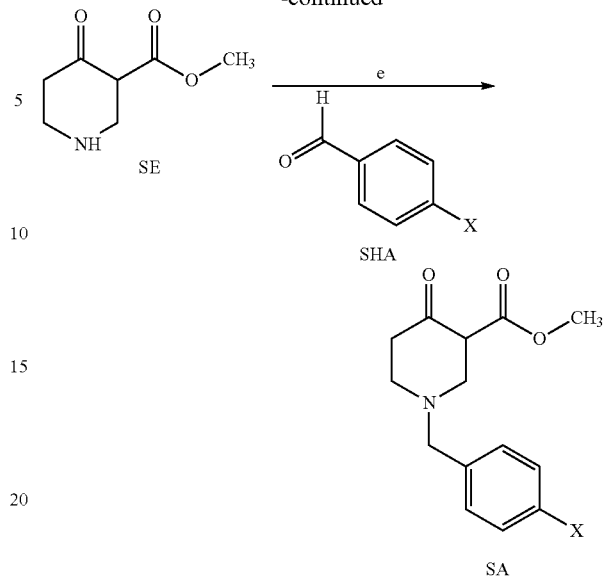

Synthesis of compounds by Scheme 1: (a) sodium carbonate, NH$_3$, ethanol, 70° C. 5 h; (b) Et$_3$N, toluene, reflux, 80° C. 8 h; (c) RBr, K$_2$CO$_3$, DMF, 100° C., 12 h; (d) DMF, Et$_3$N; (e) NaBH(OAc)$_3$, CH$_2$Cl$_2$, 30° C./4 h.

A general synthetic scheme as shown in Scheme 2, is a series of reactions that one skilled in the art may use to prepare compounds of the invention. Substituents X and Y denote various substituents that may be used for this reaction sequence and their positions on the molecule are not limited. In order to provide additional clarity X may be R$_{21}$ and Y may be R$_2$ this is in no way meant to be limiting with the number and type of substituents that may be used. The compounds denoted as SA may be prepared from the corresponding benzyl halide (SH) and ethyl 4-oxopiperidine-3-carboxylate (C$_7$H$_{11}$NO$_3$), SE (see Scheme 1). Alternatively, via a reduction with the corresponding aldehyde, SHA (see Scheme 1). The phenyl residue of SH may be replaced with a thiophene residue and optionally substituted.

Central to this chemical synthetic route is the use of thioisocyanates here shown as SSI. When Q is M1, R$_1$, R$_3$, R$_4$, R$_5$, R$_6$ and R$_7$ are simultaneously hydrogen and R$_2$ is a chlorine atom the thioisocyanate required has the chemical formula of: C$_7$H$_4$ClNS. In addition, the next step is envisioned to allow for formation of the analog shown herein as SSG via a reaction to form the guanidine residue. Treatment of SSC with a primary amine or NH$_3$ would result in the corresponding guanidine (SSG). Subsequently, SSG and SSC may be alkylated in a similar fashion as shown for the formation of SD (Scheme 1) introducing the R$_{15}$ residues. This example is not to be limiting with regard to the number and type of substituents that may be used therein. Alternative reaction conditions may be employed for the various transformations in Scheme 2. References that describe useful transformations from thioureas to guanidines are: J. Org. Chem. 1986, 51(10), p 1882-1884 and references therein and J. Med Chem. 2010, Jan. 28, 53(2) 734-44 and references sited therein. Thioisocyanates may be prepared from the corresponding amines via a reaction with thiophosgene as shown in J. Org. Chem., 1956, 21(4) p 404-405 and more recently as shown in J. Org. Chem., 2012, 8, 61-70 (Scheme 3). The precursor amines are available from chemical suppliers such as Aldrich-Aldrich, St. Louis, Mo. 63103. In addition, isocyanates such as SI made be prepared from the corresponding amines via reaction with phosgene or phosgene equivalent. There are alternative methods to prepare isocyanates: 1) Alkyl isocyanates are prepared in good to excellent yields by treatment of alcohols, thiols and trimethylsilyl ethers with triphenylphosphine/2,3-dichloro-5,6-dicyanobenzoquinone/Bu₄NOCN in acetonitrile. This method is highly selective for conversion of primary alcohols to alkyl isocyanates in the presence of secondary and tertiary alcohols, thiols and trimethysilyl ethers: *Synthesis*, 2005, 1955-1958, 2) a smooth and efficient oxidation of isonitriles to isocyanates by DMSO as the oxidant is catalyzed by trifluoroacetic anhydride; this process is complete in a few minutes, forming dimethyl sulfide as the only byproduct. The newly formed isocyanates may be used directly or isolated in high purity by solvent evaporation: *Org. Lett.*, 2011, 13, 2584-2585 and 3) acylated hydroxylamines may be converted to the corresponding isocyanates as described in: *Org. Lett.*, 2013, 15, 602-605.

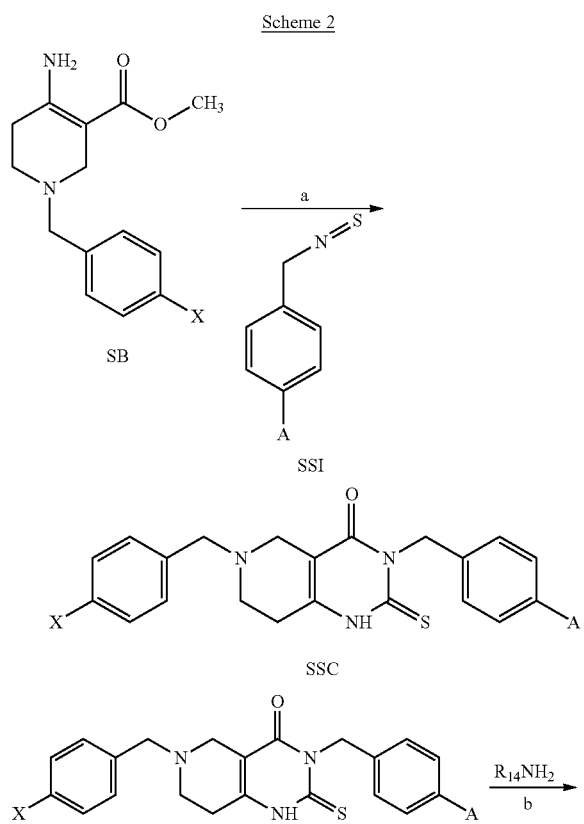

Synthesis of compounds by Scheme 2: (a) Et₃N, toluene, reflux, 80° C.; (b) Isopropyl alcohol reflux.

Scheme 3

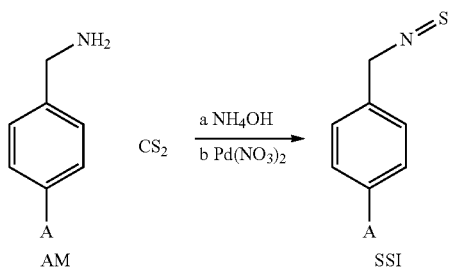

EXAMPLES

Example 1

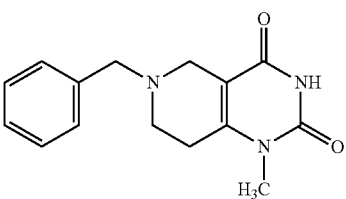

6-benzyl-1-methyl-5,6,7,8-tetrahydropyrido[4,3-d]pyrimidine-2,4(1H,3H)-dione (1)

A mixture of methyl 1-benzyl-4-oxopiperidine-3-carboxylate hydrochloride (10.0 g, 35.2 mmol) was dissolved in ethanol (150 ml), then urea (10.0 g, 167 mmol) and sodium methoxide (22.7 g, 118 mmol) were added and the mixture was heated to reflux conditions for 12 h. After cooled to 0° C., crystals formed and were separated by filtration. The crystals were suspended in water, hydrochloric acid (6.0 mol/L) was added to adjust the pH to 6.0. Stirring was continued at room temperature for 1 h, the crystals separated were isolated by filtration and dried in vacuo to prepare compound 1 (6.5 g, 72% yield). This material was used without further purification. ¹HNMR (DMSO_d6) δ 2.42 (s, 2H), 2.62 (t, J=4.8 Hz, 2H), 3.0 (s, 2H), 3.62 (s, 2H), 7.26-7.36 (m, 5H), 10.21 (s, 1H), 11.01 (s, 1H); LC-MS: m/z=258.1 (M+1).

Example 2

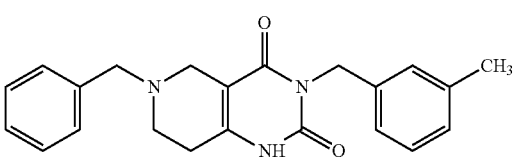

6-benzyl-3-[(3-methylphenyl)methyl]-1H, 2H, 3H, 4H, 5H, 6H, 7H, 8H-pyrido[4,3-d]pyrimidine-2,4-dione (2)

Synthesis of 2B

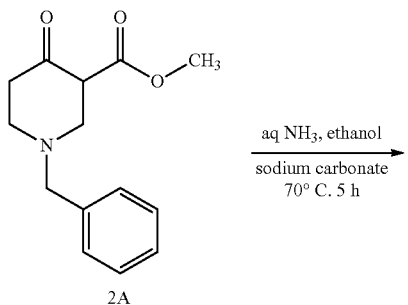

2A

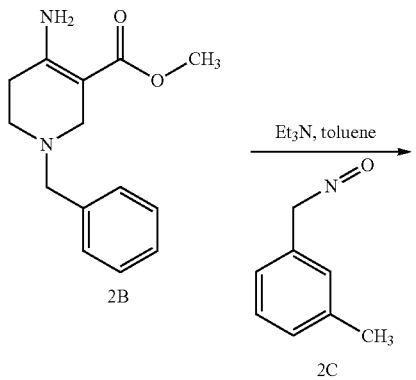

2B

A mixture of methyl 1-benzyl-4-oxopiperidine-3-carboxylate hydrochloride (2A, 8.55 g. 20.2 mmol), sodium carbonate (1.76 g) and ammonia solution (4.5 mL, 25%) in ethanol (70 ml) was heated at 70° C. for 5 h. The solution was concentrated, extracted with DCM (200 mL×2) and washed with brine. The extracts were dried over $Na_2SO_4$ and evaporated under reduced pressure to give 7.88 g of methyl 4-amino-1-benzyl-1,2,5,6-tetrahydropyridine-3-carboxylate (oil, 2B), which was directly used for next step. $^1$HNMR (400 MHz, CDCl3) δ 2.03 (m, 2H), 2.52 (m, 2H), 3.21 (s, 2H), 3.61 (s, 2H), 3.64 (s, 3H), 7.29-7.36 (m, 5H); LC-MS: m/z=247.2 (M+1).

Synthesis of 2

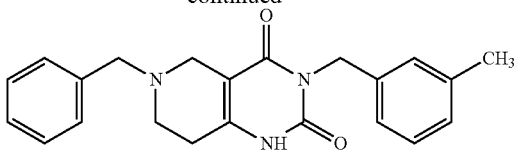

2

To a solution of methyl 4-amino-1-benzyl-1,2,5,6-tetrahydropyridine-3-carboxylate (2B, 1.7 g, 6.9 mmol) in toluene 20 mL was added 3-methylbenzylisocyanate (2C, 1.1 g, 7.5 mmol) and triethylamine (1.1 g, 10.4 mmol). The solution was heated to 80° C. for 8 h. The reaction solution was then concentrated and cooled. The formed white solid was filtered and dissolved in MeOH (20 ml). NaOMe (340 mg) was added and the mixture was refluxed overnight. Then ca 10-15 ml of methanol was removed and the precipitate was filtered. The desired product 6-benzyl-3-(3-methylbenzyl)-5,6,7,8-tetrahydropyrido[4,3-d]pyrimidine-2,4(1H,3H)-dione (2) was obtained as pale yellow solid. (0.8 g, 37%). HNMR (400 MHz, $CD_3OD$) δ 2.29 (s, 3H), 2.55 (t, J=5.2 Hz, 2H), 2.75 (t, J=5.6 Hz, 2H), 3.27 (s, 2H), 3.72 (s, 2H), 5.02 (s, 2H), 7.04-7.15 (m, 4H), 7.29-7.39 (m, 5H); LC-MS: m/z=361.9 (M+1).

Example 3

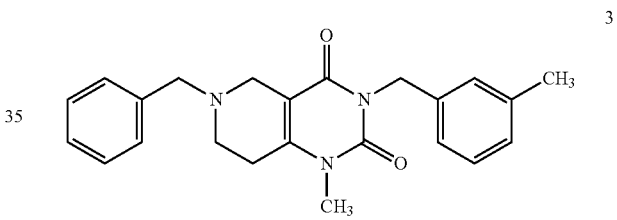

3

6-benxyl-1-methyl-3-[(3-methylphenyl)methyl]-1H, 2H, 3H, 4H, 5H, 6H, 7H, 8H-pyrido[4,3-d]pyrimidine-2,4-dione (3)

3.1 Synthesis of 3

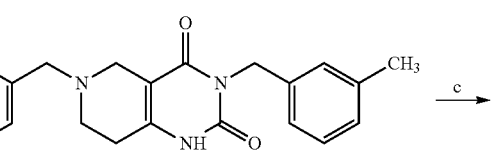

To a solution of 6-benzyl-3-(3-methylbenzyl)-5,6,7,8-tetrahydropyrido[4,3-d]pyrimidine-2,4(1H,3H)-dione (3A, 200 mg) in DMF (2 mL) was added potassium carbonate (150 mg) and methyl iodide (120 mg). The mixture was heated at 100° C. for 12 h. The water was added and the solution was extracted with EtOAc (5 ml×3). The combined extracts were washed with brine 3 times. The final product (3) was obtained by preparative TLC, 25 mg, Yield 12%. ¹HNMR (400 MHz, CD₃OD) δ 2.14 (s, 3H), 2.55-2.61 (m, 4H), 3.16 (s, 2H), 3.20 (s, 3H), 3.56 (s, 2H), 4.92 (s, 2H), 6.88-6.91 (m, 1H), 6.99-7.02 (m, 3H), 7.15-7.25 (m, 5H); LC-MS: m/z=375.9 (M+1).

Example 4

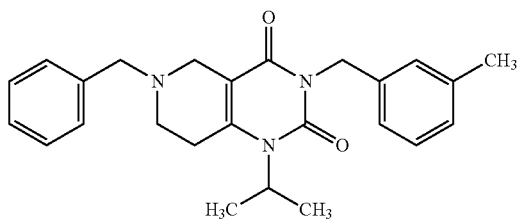

4

6-benzyl-1-isopropyl-3-(3-methylbenzyl)-5,6,7,8-tetrahydropyrido[4,3-d]pyrimidine-2,4(1H,3H)-dione (4)

Compound 4 was prepared in a similar fashion as shown in Example 3 except methyl iodide is replaced by 2-iodopropane. Yield 20%; ¹HNMR (400 MHz, CD₃OD) δ 1.18 (t, J=5.2 Hz, 6H), 2.2 (s, 3H), 2.55 (t, J=5.2 Hz, 2H), 2.65 (t, J=5.6 Hz, 2H), 3.29 (s, 2H), 3.63 (s, 2H), 5.01 (s, 2H), 5.19-5.23 (m, 1H), 6.97-7.09 (m, 4H), 7.17-7.31 (m, 5H); LC-MS: m/z=403.9 (M).

Example 5

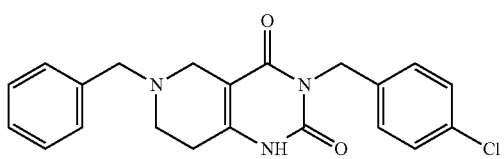

5

6-benzyl-3-(4-chlorobenzyl)-5,6,7,8-tetrahydropyrido[4,3-d]pyrimidine-2,4(1H,3H)-dione (5)

Compound 5 was prepared in a similar fashion as shown in Example 2 except 3-methylbenzylisocyanate is replaced by 4-chlorobenzyl isocyanate 97%. Yield 25%; ¹HNMR (400 MHz, CD₃OD) δ 2.53 (t, J=5.2 Hz, 2H), 2.73 (t, J=5.6 Hz, 2H), 3.3 (s, 2H), 3.71 (s, 2H), 5.03 (s, 2H), 7.24-7.36 (m, 9H); LC-MS: m/z=382.0 (M+1).

Example 6

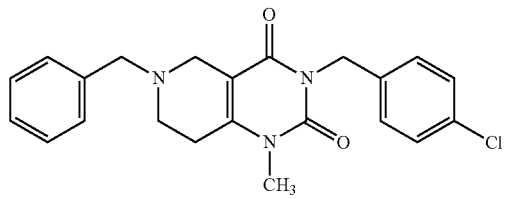

6

6-benzyl-3-(4-chlorobenzyl)-1-methyl-5,6,7,8-tetrahydropyrido[4,3-d]pyrimidine-2,4(1H,3H)-dione (6)

Compound 6 was prepared in a similar fashion as shown in Example 2 and Example 3. Notably, 3-methbenzylisocyanate is replaced by 4-chlorobenzyl isocyanate 97%. Yield 30%; ¹HNMR (400 MHz, CD₃OD) δ 2.67-2.71 (m, 4H), 3.27 (s, 2H), 3.32 (s, 3H), 3.67 (s, 2H), 5.03 (s, 2H), 7.23-7.36 (m, 9H); LC-MS: m/z=395.8 (M+1).

Example 7

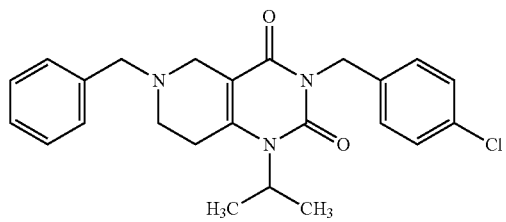

7

6-benzyl-3-(4-chlorobenzyl)-1-isopropyl-5,6,7,8-tetrahydropyrido[4,3-d]pyrimidine-2,4(1H,3H)-dione (7)

Compound 7 was prepared in a similar fashion as shown in Example 2 and Example 3. Notably, 3-methbenzylisocyanate is replaced by 4-chlorobenzyl isocyanate 97% and methyl iodide is replaced by 2-iodopropane. Yield 25%; ¹HNMR (400 MHz, CD₃OD) δ 1.29-1.3 (d, J=4 Hz, 6H), 2.66 (t, J=5.6 Hz, 2H), 2.77 (t, J=5.6 Hz, 2H), 3.37 (s, 2H), 3.74 (s, 2H), 5.13 (s, 2H), 5.29-5.35 (m, 1H), 7.27-7.41 (m, 9H); LC-MS: m/z=423.8 (M+1).

Example 8

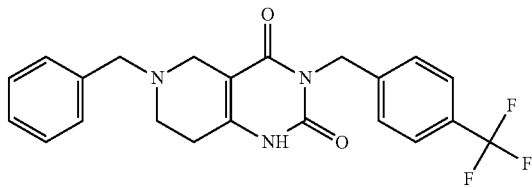

8

3-(4-(trifluoromethyl)benzyl)-6-benzyl-5,6,7,8-tetra-hydropyrido[4,3-d]pyrimidine-2,4(1H,3H)-dione (8)

Compound 8 was prepared in a similar fashion as shown in Example 2 except 3-methbenzylisocyanate is replaced by 1-isocyanatomethyl-4-trifluoromethyl-benzene. Yield 35%; $^1$HNMR (400 MHz, DMSO_d6) δ 2.49 (t, J=4.8 Hz, 2H), 2.65 (t, J=5.2 Hz, 2H), 3.07 (s, 2H), 3.63 (s, 2H), 5.01 (s, 2H), 7.27-7.35 (m, 5H), 7.44-7.46 (d, J=8 Hz, 2H), 7.65-7.67 (d, J=8 Hz, 2H); LC-MS: m/z=416.0 (M+1).

Example 9

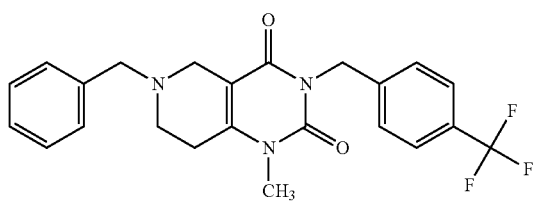

3-(4-(trifluoromethyl)benzyl)-6-benzyl-5,6,7,8-tetra-hydropyrido[4,3-d]pyrimidine-2,4(1H,3H)-dione (9)

Compound 9 was prepared in a similar fashion to Example 3 notably starting with Example 8. Yield 30%; $^1$HNMR (400 MHz, CD$_3$OD) δ 2.69-2.73 (m, 4H), 3.27 (s, 2H), 3.33 (s, 3H), 3.68 (s, 2H), 5.13 (s, 2H), 7.29-7.35 (m, 5H), 7.47-7.56 (m, 4H); LC-MS: m/z=429.8 (M+1).

Example 10

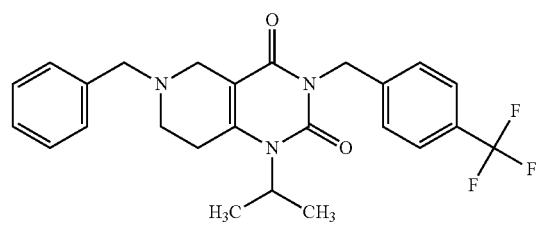

3-(4-(trifluoromethyl)benzyl)-6-benzyl-5,6,7,8-tetra-hydro-1-isopropylpyrido[4,3-d]pyrimidine-2,4(1H,3H)-dione (10)

Compound 10 was prepared in a similar procedure as shown in Example 2 and Example 3. Notably, methyl iodide is replaced by 2-iodopropane. Yield 20%; $^1$HNMR (400 MHz, CD$_3$OD) δ 1.14-1.16 (d, J=8 Hz, 6H), 2.55 (t, J=5.6 Hz, 2H), 2.66 (t, J=5.6 Hz, 2H), 3.26 (s, 2H), 3.62 (s, 2H), 5.11 (s, 2H), 5.18-5.21 (m, 1H), 7.17-7.29 (m, 5H), 7.33-7.35 (d, J=8 Hz, 2H), 7.49-7.51 (d, J=8 Hz, 2H); LC-MS: m/z=457.8 (M+1).

Example 11

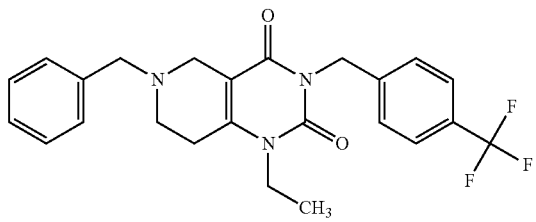

3-(4-(trifluoromethyl)benzyl)-6-benzyl-1-ethyl-5,6,7,8-tetrahydropyrido[4,3-d]pyrimidine-2,4(1H,3H)-dione (11)

Compound 11 was prepared in a similar fashion as shown in Example 2 and Example 3. Notably, in methyl iodide is replaced by iodoethane. Yield 25%; $^1$HNMR (400 MHz, CDCl3) δ 1.23-1.26 (m, 3H), 2.65-2.7 (m, 4H), 3.37 (s, 2H), 3.68 (s, 2H), 3.82-3.87 (m, 2H), 5.15 (s, 2H), 7.26-7.33 (m, 5H), 7.47-7.56 (m, 4H); LC-MS: m/z=444.2 (M+1).

Example 12

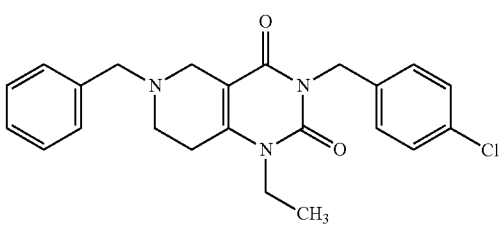

3-(4-chlorobenzyl)-6-benzyl-1-ethyl-5,6,7,8-tetrahy-dropyrido[4,3-d]pyrimidine-2,4(1H,3H)-dione (12)

Compound 12 was prepared in a similar fashion as shown in Example 2 and Example 3. Notably, methyl iodide is replaced by iodoethane. Yield 25%; $^1$HNMR (400 MHz, CDCl3) δ 1.23 (t, J=6.8H, 3H), 2.62-2.7 (m, 4H), 3.36 (s, 2H), 3.67 (s, 2H), 3.82-3.87 (m, 2H), 5.06 (s, 2H), 7.22-7.32 (m, 7H), 7.39-7.41 (d, J=8 Hz, 2H); LC-MS: m/z=410.1 (M+1).

Example 13

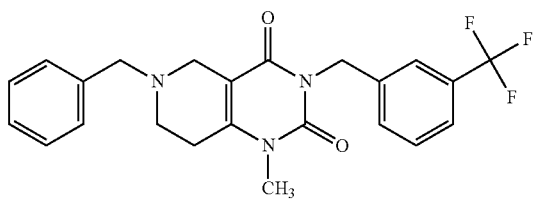

3-(4-chlorobenzyl)-6-benzyl-1-ethyl-5,6,7,8-tetrahydropyrido[4,3-d]pyrimidine-2,4(1H,3H)-dione (13)

Compound 13 was prepared similarly as given in Example 2 and Example 3. Yield 25%; ¹HNMR (400 MHz, CDCl3) δ 2.61-2.62 (d, J=4 Hz, 2H), 2.7 (t, J=4.2 Hz, 2H), 3.35 (s, 3H), 3.38 (s, 2H), 3.68 (s, 2H), 5.15 (s, 2H), 7.26-7.33 (m, 5H), 7.39 (t, J=8 Hz, 1H), 7.48-7.5 (d, J=8 Hz, 1H), 7.62-7.64 (d, J=8 Hz, 1H), 7.71 (s, 1H); LC-MS: m/z=430.1 (M+1).

Example 14

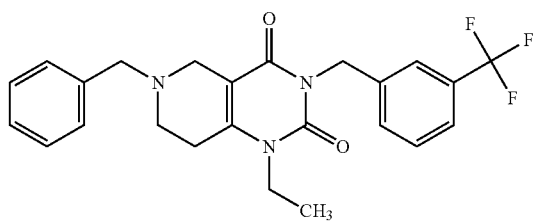

3-(3-(trifluoromethyl)benzyl)-6-benzyl-1-ethyl-5,6,7,8-tetrahydropyrido[4,3-d]pyrimidine-2,4(1H,3H)-dione (14)

Compound 14 is prepared as shown in Example 2 and Example 3. Notably, methyl iodide is replaced by Iodoethane. Yield 25%; ¹HNMR (400 MHz, CDCl3) δ 1.24 (t, J=7.2H, 3H), 2.64-2.71 (m, 4H), 3.38 (s, 2H), 3.68 (s, 2H), 3.84-3.89 (m, 2H), 5.15 (s, 2H), 7.26-7.33 (m, 5H), 7.39 (t, J=8 Hz, 1H), 7.48-7.50 (d, J=8 Hz, 1H), 7.63-7.65 (d, J=8 Hz, 1H), 7.72 (s, 1H); LC-MS: m/z=444.2 (M+1).

Example 15

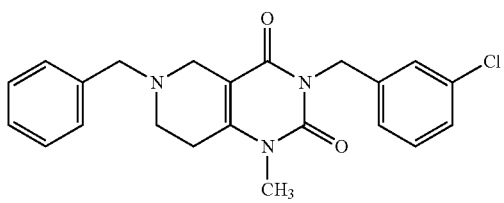

3-(3-chlorobenzyl)-6-benzyl-5,6,7,8-tetrahydro-1-methylpyrido[4,3-d]pyrimidine-2,4(1H,3H)-dione (15)

Compound 15 was prepared in a similar fashion as given in Example 2 and Example 3. Yield 25%; ¹HNMR (400 MHz, CDCl3) δ 2.68-2.75 (m, 4H), 3.38 (s, 3H), 3.42 (s, 3H), 3.71 (s, 2H), 5.26 (s, 2H), 6.98-7.0 (m, 1H), 7.14-7.16 (m, 2H), 7.28-7.36 (m, 6H); LC-MS: m/z=396.2 (M+1).

Example 16

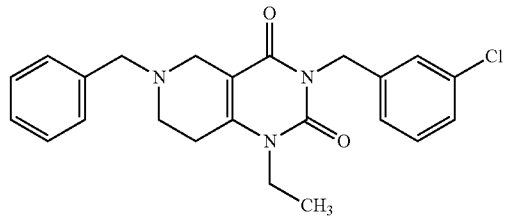

6-Benzyl-3-[(3-chlorophenyl)methyl]-1-ethyl-1H,2H,3H,4H,5H,6H,7H,8H,-pyrido[4,3-d]pyrimidine-2,4-dione (16)

Compound 16 was prepared in a similar fashion as shown in as Example 2 and Example 3. Yield 25%; ¹HNMR (400 MHz, CDCl3) δ 1.26 (t, J=7.2H, 3H), 2.71-2.75 (m, 4H), 3.41 (s, 2H), 3.71 (s, 2H), 3.87-3.89 (m, 2H), 5.26 (s, 2H), 6.97-6.99 (m, 1H), 7.14-7.16 (m, 2H), 7.27-7.36 (m, 6H); LC-MS: m/z=410.1 (M+1).

Example 17

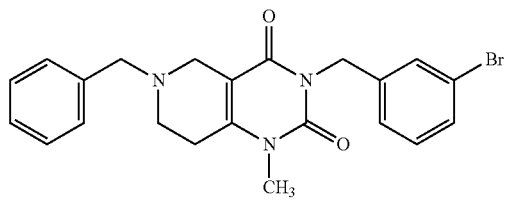

6-benzyl-3-(3-bromobenzyl)-1-methyl-5,6,7,8-tetrahydropyrido[4,3-d]pyrimidine-2,4(1H,3H)-dione (17)

Compound 17 was prepared in a similar fashion as shown in Example 2 and Example 3. Yield 30%; ¹HNMR (400 MHz, CDCl3) δ 2.62-2.63 (d, J=4 Hz, 2H), 2.71 (t, J=5.2 Hz, 2H), 3.34 (s, 3H), 3.38 (s, 2H), 3.69 (s, 2H), 5.07 (s, 2H), 7.14 (t, J=8 Hz, 1H), 7.26-7.39 (m, 7H), 7.58 (s, 1H); LC-MS: m/z=440.1(M+1).

Example 18

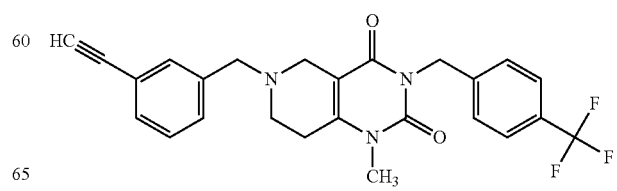

6-(3-ethynylbenzyl)-1-methyl-3-(4-(trifluoromethyl)
benzyl)-5,6,7,8-tetrahydropyrido[4,3-d]pyrimidine-
2,4(1H,3H)-dione (18)

Compound 18 was prepared in a similar fashion as shown in Example 2 and Example 3. Yield 20%; $^1$HNMR (400 MHz, CDCl3) δ 2.62-2.63 (d, J=4 Hz, 2H), 2.69 (d, J=5.2 Hz, 2H), 3.07 (s, 1H), 3.35 (s, 5H), 3.64 (s, 2H), 5.15 (s, 2H), 7.27-7.33 (m, 2H), 7.39-7.41 (d, J=8 Hz, 1H), 7.48 (s, 1H), 7.52-7.54 (d, J=8 Hz, 4H); LC-MS: m/z=454.1 (M+1).

Example 19

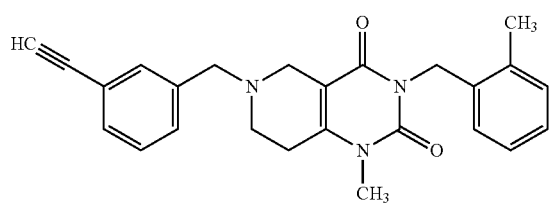

6-(3-ethynylbenzyl)-1-methyl-3-(2-methylbenzyl)-5,
6,7,8-tetrahydropyrido[4,3-d]pyrimidine-2,4(1H,
3H)-dione (19)

Compound 19 was prepared in a similar fashion as shown in Example 2 and Example 3. Yield 20%; $^1$HNMR (400 MHz, CDCl3) δ 2.44 (s, 3H), 2.62-2.63 (d, J=4 Hz, 2H), 2.69 (d, J=5.2 Hz, 2H), 3.07 (s, 1H), 3.34 (s, 3H), 3.38 (s, 2H), 3.65 (s, 2H), 5.13 (s, 2H), 7.01-7.02 (d, J=4 Hz, 1H), 7.08-7.12 (m, 3H), 7.26-7.32 (m, 2H), 7.39-7.41 (d, J=8 Hz, 1H), 7.48 (s, 1H); LC-MS: m/z=400.1 (M+1).

Example 20

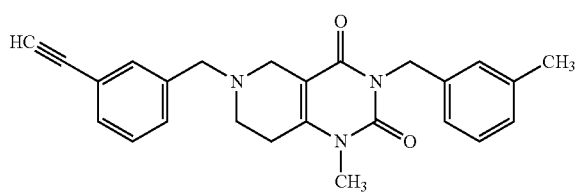

6-(3-ethynylbenzyl)-1-methyl-3-(3-methylbenzyl)-5,
6,7,8-tetrahydropyrido[4,3-d]pyrimidine-2,4(1H,
3H)-dione (20)

Compound 20 was prepared in a similar fashion as shown in Example 2 and Example 3. Yield 20%; $^1$HNMR (400 MHz, CDCl3) δ 2.31 (s, 3H), 2.62 (s, 2H), 2.7 (s, 2H), 3.07 (s, 1H), 3.35 (s, 3H), 3.38 (s, 2H), 3.67 (s, 2H), 5.09 (s, 2H), 7.04-7.06 (d, J=8 Hz, 1H), 7.15-7.19 (m, 1H), 7.26-7.35 (m, 4H), 7.4-7.42 (d, J=8 Hz, 1H), 7.48 (s, 1H); LC-MS: m/z=400.1 (M+1).

Example 21

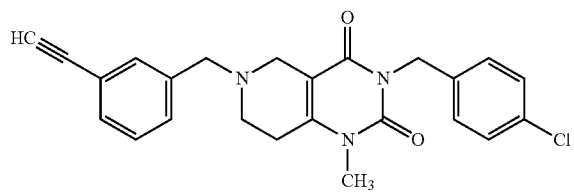

3-(4-chlorobenzyl)-6-(3-ethynylbenzyl)-1-methyl-5,
6,7,8-tetrahydropyrido[4,3-d]pyrimidine-2,4(1H,
3H)-dione (21)

Compound 21 was prepared in a similar fashion as Example 2 and Example 3. Yield 20%; $^1$HNMR (400 MHz, CDCl3) δ 2.62 (s, 2H), 2.7 (s, 2H), 3.07 (s, 1H), 3.35 (s, 5H), 3.66 (s, 2H), 5.08 (s, 2H), 7.23-7.32 (m, 4H), 7.39-7.41 (d, J=8 Hz, 3H), 7.48 (s, 1H); LC-MS: m/z=420.1 (M+1).

Example 22

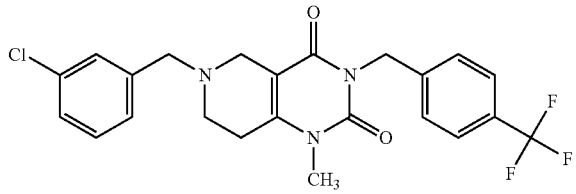

6-(3-chlorobenzyl)-1-methyl-3-(4-(trifluoromethyl)
benzyl)-5,6,7,8-tetrahydropyrido[4,3-d]pyrimidine-
2,4(1H,3H)-dione (22)

Compound 22 was prepared in a similar fashion as shown in Example 2 and Example 3. Yield 20%; $^1$HNMR (400 MHz, CDCl3) δ 2.63-2.64 (d, J=4 Hz, 2H), 2.71 (t, J=5.2 Hz, 2H), 3.36 (s, 5H), 3.65 (s, 2H), 5.16 (s, 2H), 7.19-7.26 (m, 3H), 7.35 (s, 1H), 7.52-7.57 (m, 4H); LC-MS: m/z=464.1 (M+1).

Example 23

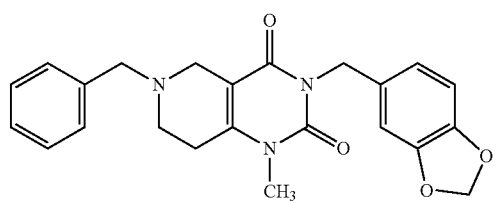

3-(benzo[d][1,3]dioxol-5-ylmethyl)-6-benzyl-1-methyl-5,6,7,8-tetrahydropyrido[4,3-d]pyrimidine-2,4(1H,3H)-dione (23)

Compound 23 was prepared in a similar fashion as shown in Example 2 and Example 3. Yield 30%; ¹HNMR (400 MHz, CDCl3) δ 2.58-2.59 (d, J=4 Hz, 2H), 2.68 (t, J=5.2 Hz, 2H), 3.33 (s, 3H), 3.36 (s, 2H), 3.67 (s, 2H), 5.02 (s, 2H), 5.88 (s, 2H), 6.69-6.71 (d, J=8 Hz, 1H), 6.95-6.98 (m, 2H), 7.27-7.32 (m, 5H); LC-MS: m/z=406.1 (M+1).

Example 24

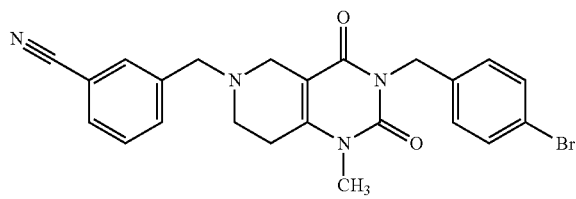

3-((3-(4-bromobenzyl)-1-methyl-2,4-dioxo-1,2,3,4,7,8-hexahydropyrido[4,3-d]pyrimidin-6(5H)-yl)methyl)benzonitrile (24)

Compound 24 was prepared in a similar fashion as shown in Example 2 and Example 3. Yield 25%; ¹HNMR (400 MHz, CDCl3) δ 2.64-2.65 (d, J=4 Hz, 2H), 2.72 (t, J=5.2 Hz, 2H), 3.33 (s, 2H), 3.37 (s, 3H), 3.7 (s, 2H), 5.06 (s, 2H), 7.34-7.45 (m, 5H), 7.56-7.58 (d, J=8 Hz, 2H), 7.66 (s, 1H); LC-MS: m/z=465.1(M+1).

Example 25

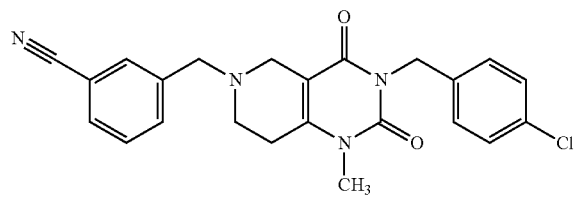

3-((3-(4-chlorobenzyl)-1-methyl-2,4-dioxo-1,2,3,4,7,8-hexahydropyrido[4,3-d]pyrimidin-6(5H)-yl)methyl)benzonitrile (25)

Compound 25 was prepared in a similar fashion as shown in Example 2 and Example 3. Yield 20%; ¹HNMR (400 MHz, CDCl3) δ 2.65 (s, 2H), 2.73 (s, 2H), 3.34 (s, 2H), 3.37 (s, 3H), 3.71 (s, 2H), 5.08 (s, 2H), 7.26 (t, J=8 Hz, 2H), 7.4-7.46 (m, 3H), 7.57-7.59 (d, J=8 Hz, 2H), 7.67 (s, 1H); LC-MS: m/z=421.1 (M+1).

Example 26

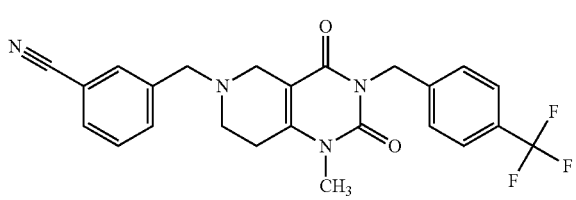

3-((1-methyl-2,4-dioxo-3-(4-(trifluoromethyl)benzyl)-1,2,3,4,7,8-hexahydropyrido[4,3-d]pyrimidin-6(5H)-yl)methyl)benzonitrile (26)

Compound 26 was prepared in a similar fashion as shown in Example 2 and Example 3. Yield 20%; ¹HNMR (400 MHz, CDCl3) δ 2.66-2.67 (d, J=4 Hz, 2H), 2.73 (t, J=5.2 Hz, 2H), 3.34 (s, 2H), 3.38 (s, 3H), 3.71 (s, 2H), 5.16 (s, 2H), 7.43 (t, J=8 Hz, 1H), 7.52-7.58 (m, 6H), 7.67 (s, 1H); LC-MS: m/z=455.1 (M+1).

Example 27

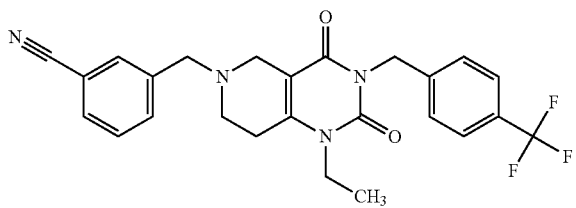

3-((1-ethyl-2,4-dioxo-3-(4-(trifluoromethyl)benzyl)-1,2,3,4,7,8-hexahydropyrido[4,3-d]pyrimidin-6(5H)-yl)methyl)benzonitrile (27)

Compound 27 was prepared as shown in Example 2 and Example 3. Notably, methyl iodide is replaced by iodoethane. Yield 15%; ¹HNMR (400 MHz, CDCl3) δ 1.27 (t, J=5.6 Hz, 3H), 2.68-2.74 (m, 4H), 3.34 (s, 2H), 3.7 (s, 2H), 3.86-3.91 (m, 2H), 5.16 (s, 2H), 7.44 (t, J=8 Hz, 1H), 7.52-7.58 (m, 6H), 7.67 (s, 1H); LC-MS: m/z=469.1 (M+1).

Example 28

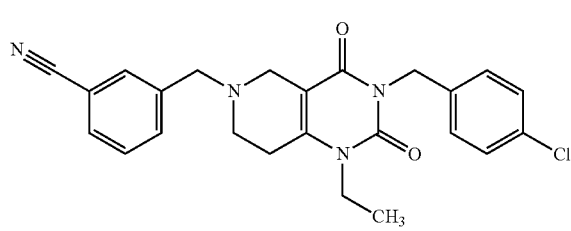

3-((3-(4-chlorobenzyl)-1-ethyl-2,4-dioxo-1,2,3,4,7,8-hexahydropyrido[4,3-d]pyrimidin-6(5H)-yl)methyl)benzonitrile (28)

Compound 28 was prepared in a similar fashion as shown in Example 2 and Example 3. Notably, methyl iodide is replaced by iodoethane. Yield 20%; $^1$HNMR (400 MHz, CDCl3) δ 1.26 (t, J=7.2 Hz, 3H), 2.67-2.73 (m, 4H), 3.33 (s, 2H), 3.7 (s, 2H), 3.85-3.9 (m, 2H), 5.07 (s, 2H), 7.25 (t, J=8.4 Hz, 2H), 7.39-7.45 (m, 3H), 7.56-7.58 (d, J=8 Hz, 2H), 7.67 (s, 1H); LC-MS: m/z=435.2 (M+1).

Example 29

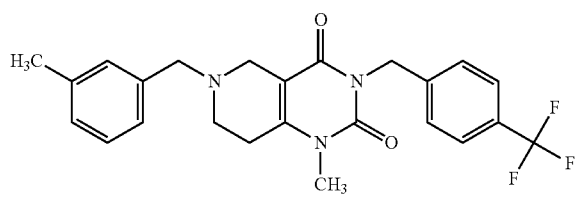

1-methyl-6-(3-methylbenzyl)-3-(4-(trifluoromethyl)benzyl)-5,6,7,8-tetrahydropyrido[4,3-d]pyrimidine-2,4(1H,3H)-dione (29)

Compound 29 was prepared in a similar fashion as shown in Example 2 and Example 3. Yield 25%; $^1$HNMR (400 MHz, CD$_3$OD) δ 2.68-2.72 (m, 4H), 3.27 (s, 2H), 3.33 (s, 3H), 3.68 (s, 2H), 5.16 (s, 2H), 7.29-7.35 (m, 5H), 7.47-7.56 (m, 4H); LC-MS: m/z=444.2 (M+1).

Example 30

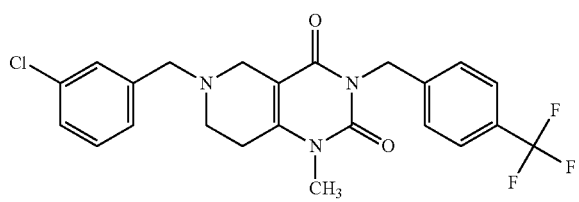

6-[(3-chlorophenyl)methyl]-1-methyl-3-{[4-(trifluoromethyl)phenyl]methyl}-1H,2H,3H,4H, 5H,6H,7H,8H-pyrido{4,3-d}pyrimidine-2,4-dione (30)

Compound 30 was prepared in a similar fashion as shown in Example 2 and Example 3. Yield 23%; LC-MS: m/z=464.1 (M+1).

Biological Assays and Data

Compounds of the present invention may be tested on human derived cancer cells.

Cancer cell lines, HCT116 (human colon cancer) or MDA-MB-231 (MDA 231, human breast adenocarcinoma) were dispensed in 100 ul of cell suspension in a 96-well plate. The plate was incubated for 24 hours in a humidified incubator (37° C., 5% CO$_2$). The compound from the present invention, at the appropriate test concentrations, are added to the culture media of the plate. The plate is incubated for 48 hours. CCK-8 (10 ul, see below) is added to each well. The plate is incubated from 1-4 h under conditions as described above, and the absorbance at 450 nm and 650 nm is measured with a plate reader.

Cell Counting Kit-8 (CCK-8) allows sensitive colorimetric assays for the determination of the number of viable cells in the proliferation and cytotoxicity assays. Cell Counting was by CCK-8 using WST-8 (2-(2-methoxy-4-nitrophenyl)-3-(4-nitrophenyl)-5-(2,4-disulfophenyl)-2H-tetrazolium, monosodium salt), which produces a water-soluble formazan dye upon bioreduction in the presence of an electron carrier, 1-Methoxy PMS. CCK-8 solution is added directly to the cells. WST-8 is bioreduced by cellular dehydrogenases to an orange formazan product that is soluble in tissue culture medium. The amount of formazan produced is directly proportional to the number of living cells.

Biological activity on human cancer cells for selected examples is provided in Table 1. Compounds of the invention show significant and unanticipated improvements in potency on human cancer lines in comparison to TIC10 (11-benzyl-7-[(2-methylphenyl)methyl]-2,5,7,11-tetraazatricyclo[7.4.0.0$^{2,6}$]trideca-1(9),5-dien-8-one).

TABLE 1

Biological activity data on human cancer cells for select analogs

| Compound/Example # | EC$_{50}$ (uM, HCT116) | EC$_{50}$ (uM, MDA 231) |
|---|---|---|
| TIC10 | 2.8 | 3.0 |
| 1 | ND | >100 |
| 2 | 3.0 | 3.6 |
| 3 | 0.18 | 0.24 |
| 4 | 2.0 | 4.1 |
| 5 | 2.7 | 10 |
| 6 | 0.26 | 0.29 |
| 7 | 6.6 | 14 |
| 8 | 2.6 | 1.3 |
| 9 | 0.31 | 1.1 |
| 10 | 7.1 | 4.0 |
| 11 | 0.75 | 0.23 |
| 12 | 0.81 | 1.1 |
| 13 | 1.4 | 1.1 |
| 14 | 2.5 | 1.0 |
| 15 | 3.0 | 2.1 |
| 16 | 1.8 | 3.3 |
| 17 | 1.1 | 0.86 |
| 18 | 1.4 | 0.68 |
| 19 | 1.5 | 1.1 |
| 20 | 1.0 | 0.55 |
| 21 | 1.4 | 0.63 |
| 22 | 0.1 | 0.29 |
| 23 | 2.5 | 2.6 |
| 24 | 0.022 | 0.11 |
| 25 | 0.74 | 0.19 |
| 26 | 0.50 | 0.085 |
| 27 | 1.9 | 0.22 |
| 28 | 0.21 | 0.022 |
| 29 | ND | 1.4 |
| 30 | 0.098 | 0.29 |

In a similar fashion to the above studies on human cancer cells (HCT116 and MDA 231), compounds of the present invention were studied on a human cancer cell line, SUM159 (SUM159 SUM-159 was derived from a primary human anaplastic breast carcinoma and is a basal breast cancer cell line).

Biological activity on human cancer cells for selected examples is provided in Table 2 and in FIG. 1. A similar experimental procedure with human cancer cells (SUM159) to that described above for HCT 116 with the notable change in that the compound incubation with the cells is for 72 hours. Examples #25 and #26 of the invention show significant and unanticipated improvements in potency on human cancer lines in comparison to TIC10 (11-benzyl-7-[(2-methylphenyl)methyl]-2,5,7,11-tetraazatricyclo[7.4.0.0$^{2,6}$]trideca-1(9),5-dien-8-one).

TABLE 2

Biological activity data on human cancer cells (SUM159) for select analogs

| Compound/Example # | EC$_{50}$ (uM, SUM159) |
|---|---|
| TIC10 | 1.4 |
| 25 | 0.014 |
| 26 | 0.017 |

All publications and patent applications cited in the specification are herein incorporated by reference in their entirety. Although the foregoing invention has been described in some detail by way of illustration and example, it will be readily apparent to those of ordinary skill in the art in light of the teachings of this invention that certain changes and modifications may be made thereto without departing from the spirit or scope of the appended claims.

What is claimed is:

1. A compound of Formula (I):

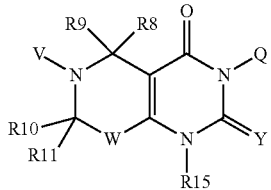

(I)

wherein:

Q is independently selected from the group consisting of

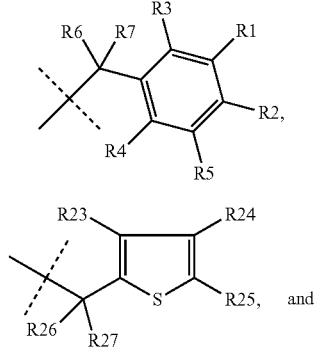

M1

M2

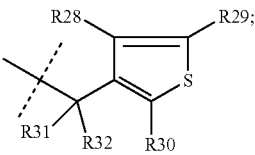

M3

V is independently selected from the group consisting of:

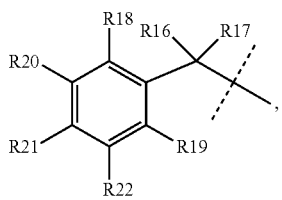

V1

V2

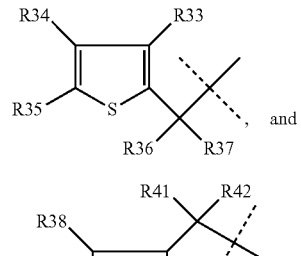

V3

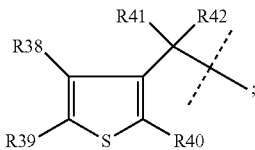

W is absent or —C(R$_{12}$R$_{13}$)—;

Y is independently selected from the group consisting of oxygen, sulphur, and —NR$_{14}$;

R$_1$, R$_2$, R$_3$, R$_4$, and R$_5$ are independently selected from the group consisting of hydrogen, halogen, —CN, —S(O)$_2$R$_{43}$, —NO$_2$, —NR$_{44}$R$_{45}$, —OH, —SH, —SR$_{46}$, (C1-C3)haloalkyloxy, (C1-C4)alkoxy, (C1-C6)alkyl, (C3-C6)cycloalkyl, (C2-C6)alkynyl, (C2-C6)alkenyl and (C1-C6)haloalkyl; or alternatively, R$_1$ and R$_2$ are taken together with the carbon atoms to which they are attached to form a 4-6 membered ring, with the proviso that R$_1$, R$_2$, R$_3$, R$_4$ and R$_5$ are not simultaneously hydrogen;

R$_{23}$, R$_{24}$, R$_{25}$, R$_{28}$, R$_{29}$ and R$_{30}$ are independently selected from the group consisting of hydrogen, halogen, —CN, —S(O)$_2$R$_{43}$, —NO$_2$, —NR$_{44}$R$_{45}$, —OH, —SH, —SR$_{46}$, (C1-C3)haloalkyloxy, (C1-C4)alkoxy, (C1-C6)alkyl, (C3-C6)cycloalkyl, (C2-C6)alkynyl, (C2-C6)alkenyl and (C1-C6)haloalkyl; or alternatively, R$_{24}$ and R$_{25}$ are taken together with the carbon atoms to which they are attached to form a ring;

R$_{28}$ and R$_{29}$ may be taken together with the carbon atoms to which they are attached to form a ring;

R$_6$ and R$_7$ are hydrogen;

R$_8$, R$_9$, R$_{10}$, R$_{11}$, R$_{12}$, R$_{13}$, R$_{16}$, R$_{17}$, R$_{26}$, R$_{27}$, R$_{31}$, R$_{32}$, R$_{36}$, R$_{37}$, R$_{41}$ and R$_{42}$ are each independently selected from the group consisting of hydrogen, halogen, —CN, —S(O)$_2$R$_{43}$, —NO$_2$, —NRR, —OH, —SH, —SR$_{46}$, (C1-C3)haloalkyloxy, (C1-C4)alkoxy, (C1-C6)alkyl, (C3-C6)cycloalkyl, (C2-C6)alkynyl, (C2-C6)alkenyl and (C1-C6)haloalkyl;

R<sub>14</sub> and R<sub>15</sub> are independently selected from the group consisting of hydrogen, halogen, —CN, —S(O)$_2$R$_{43}$, —NO$_2$, —NR$_{44}$R$_{45}$, —OH, —SH, —SR$_{46}$, —S(O)$_2$ R$_{43}$, (C1-C3)haloalkyloxy, (C1-C4)alkoxy, (C1-C6)alkyl, (C3-C6)cycloalkyl, (C2-C6)alkynyl, (C2-C6)alkenyl and (C1-C6)haloalkyl, —C(NH)NH$_2$, —C(O)R$_{43}$, —C(O)OR$_{46}$;

R$_{18}$, R$_{19}$, R$_{20}$, R$_{21}$ and R$_{22}$ are independently selected from the group consisting of the following: hydrogen, halogen, (C1-C6)alkyl, (C3-C9)cycloalkyl, (C3-C9)cycloalkyl(C1-C6)alkyl, (C1-C6)haloalkyl, —OH, —SH, (C1-C6)alkoxy, —NR$_{44}$R$_{45}$, (C3-C9)cycloalkyl(C2-C6)alkynyl, (C4-C8)cycloalkenyl, (C4-C8)cycloalkenyl(C1-C6)alkyl, aryl, optionally substituted heterocyclyl with 5-10 ring atoms, optionally substitued 4- or 5-membered heterocyclic ring, optionally substituted 6-membered heterocyclic ring, —CN, —NO$_2$, —SR$_{46}$, —C(O)OH, —C(O)OR$_{46}$, —OC(O)OR$_{46}$, (C2-C6)alkynyl, (C2-C8)alkenyl, (C1-C6)haloalkyoxy, —S(O)$_2$ OR$_{46}$, —SO$_2$NR$_{44}$R$_{45}$, —S(O)$_2$R$_{43}$, —NR$_{47}$S(O)$_2$R$_{43}$, —C(O)NR$_{44}$R$_{45}$, —C(O)R$_{43}$, and —NR$_{47}$C(O)R$_{43}$; or alternatively, R$_{20}$ and R$_{21}$ are taken together with the carbon atoms to which they are attached to form a ring;

R$_{33}$, R$_{34}$, R$_{35}$, R$_{38}$, R$_{39}$ and R$_{40}$ are independently selected from the group consisting of the following: hydrogen, halogen, (C1-C6)alkyl, (C3-C9)cycloalkyl, (C3-C9)cycloalkyl(C1-C6)alkyl, (C1-C6)haloalkyl, —OH, —SH, (C1-C6)alkoxy, —NR$_{44}$R$_{45}$, (C3-C9)cycloalkyl(C2-C6)alkoxy, (C4-C8)cycloalkenyl, (C4-C8)cycloalkenyl(C1-C6)alkyl, aryl, optionally substituted heteroaryl with 5-10 ring atoms, optionally substituted 4- or 5-membered heterocyclic ring, optionally substituted 6-membered heterocyclic rig, —CN, —NO$_2$, —SR$_{46}$, —C(O)OH, —C(O)OR$_{46}$, —OC(O)OR$_{46}$, (C2-C6)alkynyl, (C2-C8)alkenyl, (C1-C6)haloalkyoxy, —S(O)$_2$OR$_{46}$, —SO$_2$NR$_{44}$R$_{45}$, —S(O)$_2$R$_{43}$, —NR$_{47}$S(O)$_2$R$_{43}$, —C(O)NR$_{44}$R$_{45}$, —C(O)R$_{43}$, and —NR$_{47}$C(O)R$_{43}$; or alternatively, R$_{34}$ and R$_{35}$ are taken together with the carbon atoms to which they are attached to form a ring;

R$_{38}$ and R$_{39}$ are taken together with the carbon atoms to which they are attached to form a ring;

R$_{43}$ is independently selected from the group consisting of hydrogen, (C1-C6)alkyl, (C3-C9)cycloalkyl, (C1-C6) haloalkyl, (C2-C6)alkynyl, (C2-C8)alkenyl, (C1-C6) haloalkyoxy, aryl, optionally substituted heteroaryl with 5-10 ring atoms and optionally substituted 4- or 5-membered heterocyclic ring, optionally substituted 6-membered heterocyclic ring, and —NR$_{44}$R$_{45}$;

R$_{44}$, R$_{45}$ and R$_{47}$ are independently selected from the group consisting of hydrogen, (C1-C6)alkyl, (C3-C9) cycloalkyl, (C1-C6)haloalkyl, (C2-C6)alkynyl, (C2-C8)alkenyl, (C1-C6)haloalkyoxy, aryl, optionally substituted heteroaryl with 5-10 ring atoms and optionally substituted 4- or 5-membered heterocyclic ring, optionally substituted 6-membered heterocyclic ring; R$_{44}$ and R$_{45}$ together with the nitrogen atom to which they are attached may form a ring;

R$_{46}$ is independently selected from the group consisting of hydrogen, (C1-C6)alkyl, (C3-C9)cycloalkyl, (C1-C6) haloalkyl, (C2-C6)alkynyl, (C2-C8)alkenyl, (C1-C6) haloalkyoxy, aryl, optionally substituted heteroaryl with 5-10 ring atoms and opionally substituted 4- or 5-membered hterocyclic ring, optionally substituted 6-membered heterocyclic ring;

or a pharmaceutically acceptable salt thereof.

2. The compound of claim 1, wherein Y is oxygen; or a pharmaceutically acceptable salt thereof.

3. The compound of claim 2 wherein;

Q is M1;

V is V1;

R$_{15}$ is independently selected from the group consisting of hydrogen, —CN, —S(O)$_2$R$_{43}$, —NO$_2$, —NR$_{44}$R$_{45}$, —OH, —SR$_{46}$, —S(O)$_2$R$_{43}$, (C1-C3)haloalkyloxy, (C1-C4)alkoxy, (C1-C6)alkyl, (C3-C6)cycloalkyl, (C2-C6)alkynyl, (C2-C6)alkenyl and (C1-C6)haloalkyl, —C(NH)NH$_2$, —C(O)R$_{43}$, —C(O)OR$_{46}$;

or a pharmaceutically acceptable salt thereof.

4. The compound of claim 3 wherein;

R$_1$ is independently selected from hydrogen, fluorine and chlorine;

R$_2$ is independently selected from chlorine, bromine and —CF$_3$;

R$_3$ is independently selected from hydrogen and fluorine;

R$_{15}$ is independently selected from —CH$_3$ and —CH$_2$CH$_3$;

R$_{20}$ is —CN;

R$_4$, R$_5$, R$_6$, R$_7$, R$_8$, R$_9$, R$_{10}$, R$_{11}$, R$_{16}$, R$_{17}$, R$_{18}$, R$_{19}$, R$_{21}$, R$_{22}$ are simultaneously hydrogen;

or a pharmaceutically acceptable salt thereof.

5. A compound or a pharmaceutically acceptable salt thereof, wherein the compound is:

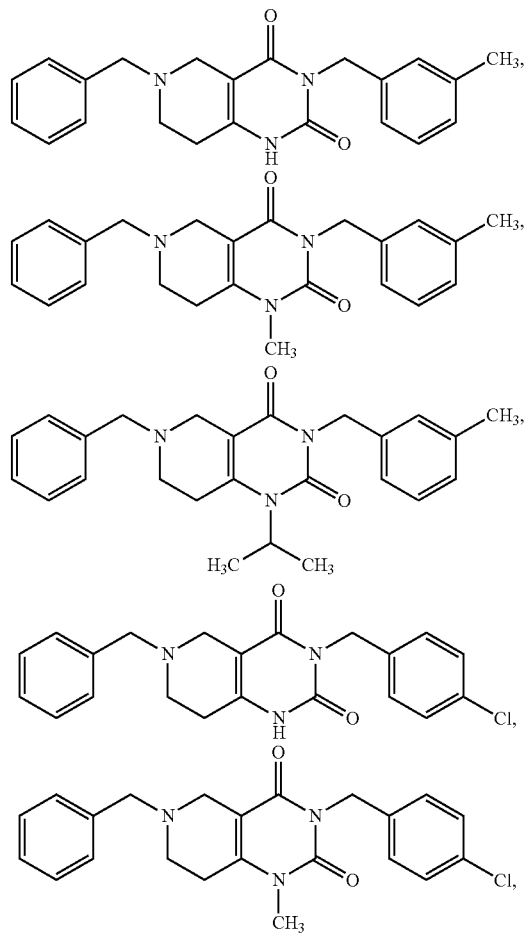

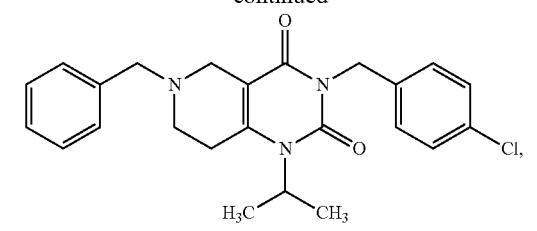
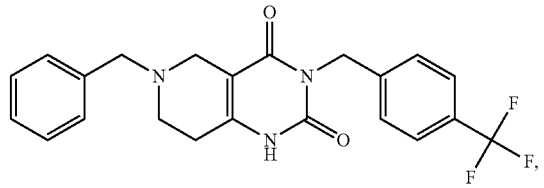
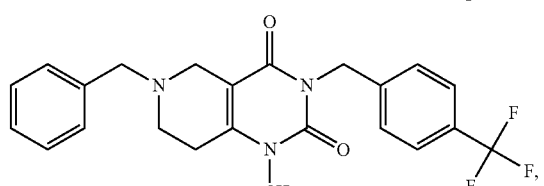
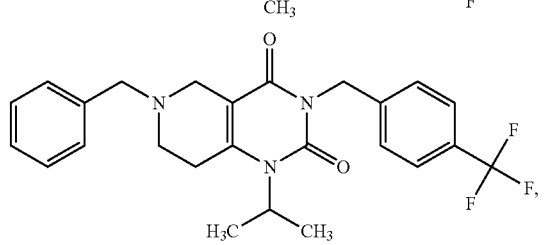
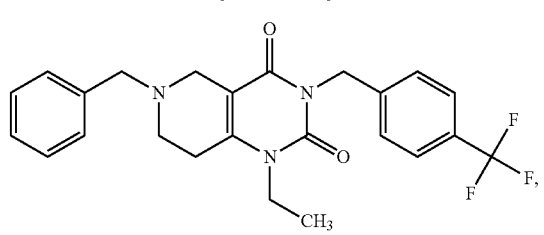
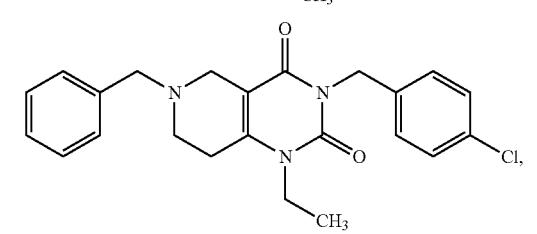
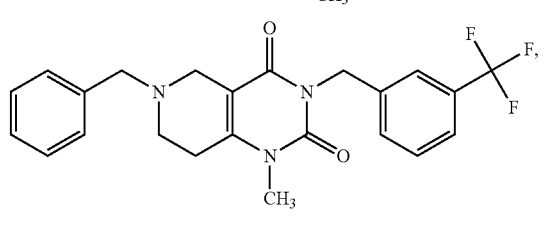
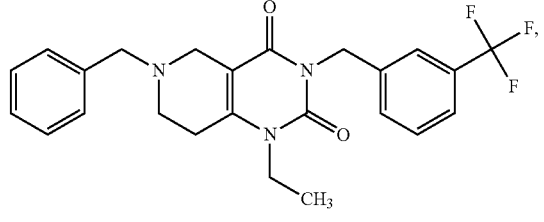
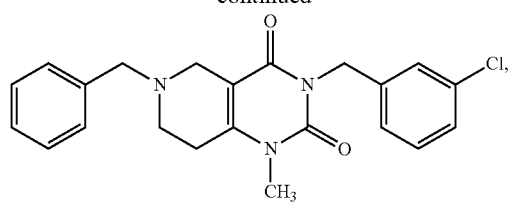
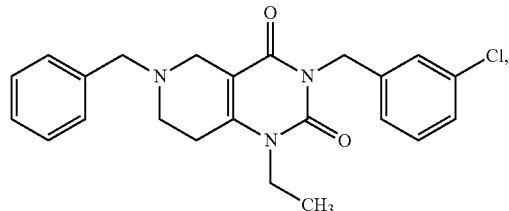
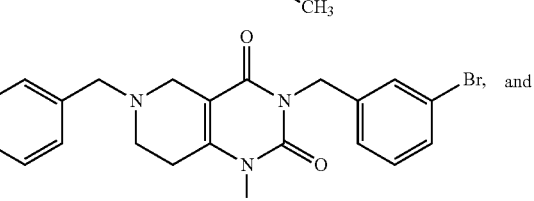
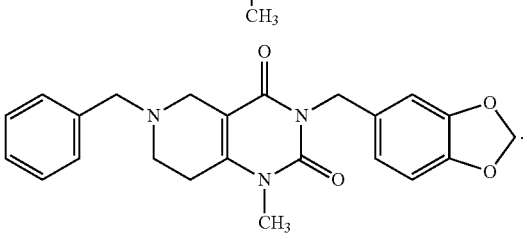
6. A compound or a pharmaceutically acceptable salt thereof, wherein the compound is:
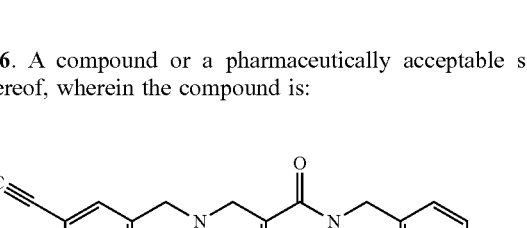
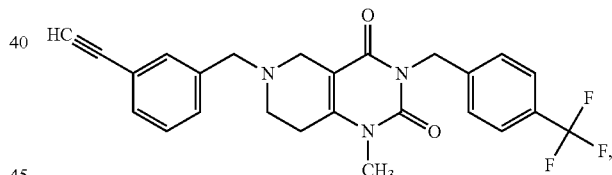
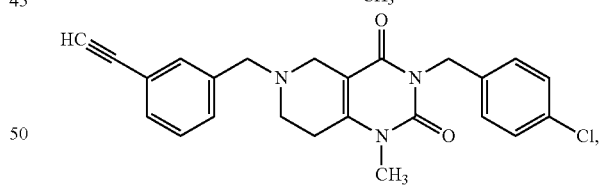
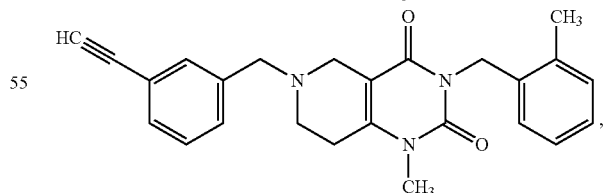
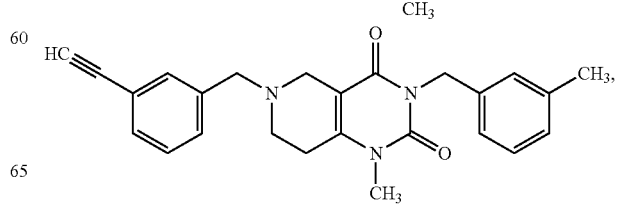

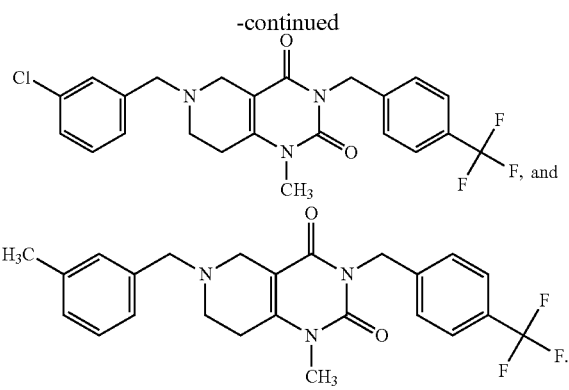

7. A compound or a pharmaceutically acceptable salt thereof, wherein the compound is:

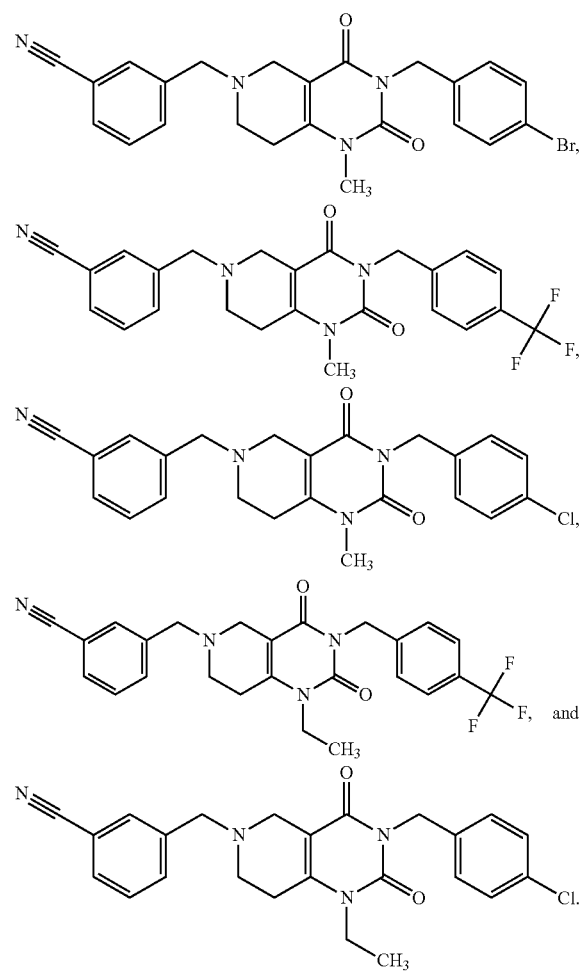

8. A method for the treatment of breast or colon cancer in a subject, comprising administering an effective amount of a compound of claim 1, or a pharmaceutically acceptable salt thereof.

9. A method for the treatment of breast or colon cancer in a subject, comprising administering an effective amount of a compound of claim 2, or a pharmaceutically acceptable salt thereof.

10. A method for the treatment of breast or colon cancer in a subject, comprising administering an effective amount of a compound of claim 3, or a pharmaceutically acceptable salt thereof.

11. A method for the treatment of breast or colon cancer in a subject, comprising administering an effective amount of a compound of claim 4, or a pharmaceutically acceptable salt thereof.

12. A method for the treatment of breast or colon cancer in a subject, comprising administering an effective amount of a compound of claim 5, or a pharmaceutically acceptable salt thereof.

13. A method for the treatment of breast or colon cancer in a subject, comprising administering an effective amount of a compound of claim 6, or a pharmaceutically acceptable salt thereof.

14. A method for the treatment of breast or colon cancer in a subject, comprising administering an effective amount of a compound of claim 7, or a pharmaceutically acceptable salt thereof.

15. A pharmaceutical composition, comprising a compound of claim 1, or a pharmaceutically acceptable salt thereof, and a pharmaceutically acceptable carrier or excipient.

16. A pharmaceutical composition, comprising a compound of claim 2, or a pharmaceutically acceptable salt thereof, and a pharmaceutically acceptable carrier or excipient.

17. A pharmaceutical composition, comprising a compound of claim 3, or a pharmaceutically acceptable salt thereof, and a pharmaceutically acceptable carrier or excipient.

18. A pharmaceutical composition, comprising a compound of claim 4, or a pharmaceutically acceptable salt thereof, and a pharmaceutically acceptable carrier or excipient.

19. A pharmaceutical composition, comprising a compound of claim 5, or a pharmaceutically acceptable salt thereof, and a pharmaceutically acceptable carrier or excipient.

20. A pharmaceutical composition, comprising a compound of claim 6, or a pharmaceutically acceptable salt thereof, and a pharmaceutically acceptable carrier or excipient.

21. A pharmaceutical composition, comprising a compound of claim 7, or a pharmaceutically acceptable salt thereof, and a pharmaceutically acceptable carrier or excipient.

* * * * *